US005344655A

United States Patent [19]

Sakai et al.

[11] Patent Number: 5,344,655

[45] Date of Patent: Sep. 6, 1994

[54] EXTERNAL APPLICATION BASE OR AUXILIARY AGENT AND EXTERNAL APPLICATION COMPOSITION FOR HUMAN BEING OR ANIMAL CONTAINING THE SAME

[75] Inventors: Yasuyuki Sakai, Tokyo; Noriyuki Suzuki, Oita; Tetsuo Kudo, Oita; Kuniomi Marumo, Oita; Toshiyuki Aizawa, Oita; Kunio Imamura, Tokyo; Shuichi Sugita, Tokyo; Kazuo Kanbayashi, Tokyo, all of Japan

[73] Assignee: Showa Denko K.K., Tokyo, Japan

[21] Appl. No.: 32,100

[22] Filed: Mar. 17, 1993

Related U.S. Application Data

[62] Division of Ser. No. 652,715.

[30] Foreign Application Priority Data

| | | | |
|---|---|---|---|
| Mar. 12, 1990 | [JP] | Japan | 2-60741 |
| Mar. 12, 1990 | [JP] | Japan | 2-62232 |
| Mar. 12, 1990 | [JP] | Japan | 2-62233 |
| Mar. 12, 1990 | [JP] | Japan | 2-62234 |

[51] Int. Cl.$^5$ .......... A61K 9/70

[52] U.S. Cl. .......... 424/443; 424/78.35; 424/78.31; 424/78.37; 424/447

[58] Field of Search .......... 424/78.31, 78.35, 78.37, 424/443, 445, 447

[56] References Cited

U.S. PATENT DOCUMENTS

| | | | |
|---|---|---|---|
| 3,632,547 | 1/1972 | Kajioka | 424/443 |
| 4,631,227 | 12/1986 | Nakamura | 424/401 |
| 5,032,403 | 7/1991 | Sinnreich | 424/78.35 |
| 5,035,893 | 7/1991 | Shioya | 424/443 |
| 5,037,656 | 8/1991 | Pitt | 424/443 |

*Primary Examiner*—Thurman K. Page
*Assistant Examiner*—Raj Bawa
*Attorney, Agent, or Firm*—Sughrue, Mion, Zinn, Macpeak & Seas

[57] ABSTRACT

A (co)polymer suitable for bases or auxiliary agents for external application (for example, hydrophilic gels, adhesives, thickeners or excipients) to be coated or plastered onto the skin or mucosa of a human being or animal, such as ointment agents (ointment, hydrogel, jelly or cream), plastering agents (molded poultice, tape agent or plaster agent), sticky bandages (sticky bandage, strap, wound strap, surgical tape, taping material, supporter), and to preparations for external application containing same.

3 Claims, No Drawings

EXTERNAL APPLICATION BASE OR AUXILIARY AGENT AND EXTERNAL APPLICATION COMPOSITION FOR HUMAN BEING OR ANIMAL CONTAINING THE SAME

This is a divisional of application Ser. No. 07/652,715 filed Feb. 8, 1991, now U.S. Pat. No. 5,254,338 issued on Oct. 19, 1993.

BACKGROUND OF THE INVENTION

1. Field of the Invention

The present invention relates to a (co)polymer suitable for bases or auxiliary agents for external application (for example, hydrophilic gels, tackifiers, thickeners or excipients) to be coated or plastered onto the skin or mucosa of a human being or animal, such as ointment agents (ointment, hydrogel, jelly or cream), plastering agents (molded poultice, tape agent or plaster agent), sticky (or adhesive) bandages (sticky bandage, strap, wound strap, surgical tape, taping material, supporter), and to preparations for external application containing same.

2. Description of the Related Art

The various pharmacologically active ingredients currently used for the therapy or prophylaxis of diseases of human beings or animals, or for maintaining health and body energy, include many which require administration or application 3 to 4 times per day, because of a short persistency of the action thereof. These ingredients, although having excellent therapeutical effects, are known to frequently cause not only the problems of a cumbersome administration or a non-compliance on the patient's side, and a laborous and time-consuming administration, but also side effects or drug problems due to an excessive administration of these pharmacologically active ingredients.

As the means for solving such problems, many attempts have been made in the prior art to formulate pharmacologically active ingredients in external applications such as ointments, poultices, and tape agents to thereby obtain a persistent therapeutical effect by an absorption through the skin.

Among the above, ointments are used for the therapy of local diseases such as inflammation or various skin diseases, or for systemic diseases such as angina pectoris, and are frequently used as a method of obtaining therapeutical effects at the afflicted sites while avoiding the systemic side-effects caused by oral agents.

In the prior art, as the base of these ointments, there are used oily bases such as vegetable oils, lard, and glycerine, and water-soluble bases such as macrogols, but the former cause problems such as a stickiness on the skin, oily feeling at the coated surface, a bad odor, or a restriction of the formulation of water-soluble pharmacologically active ingredients, and the latter cause problems such as a poor absorbability of the pharmacologically active ingredients, and do not provide the required therapeutical effect.

To solve these problems, hydrogel bases containing water-soluble polymers such as polyacrylic acid, starch, gum tragacanth, alginic acid, and cellulose derivatives formulated therein are employed. Particularly, hydrous gel bases containing water and polyacrylic acid, alcohols, amines formulated therein have an excellent absorbability of pharmacologically active ingredients, and are used for the amelioration of the therapeutical effects of antiinflammatory agents such as indomethacin and ketoprofen, and adrenocortical hormones such as fluocinolone acetanide (e.g., Chem. Pharm. Bull., 29, 2338 (1981) and Japanese Unexamined Patent Publication (Kokai) No. 58-83621).

Nevertheless, since the salts of polyacrylic acid are anionic polymers, they cause problems such as the forming of complexes with basic pharmacologically active ingredients, to thereby lower the absorbability of the pharmacologically active ingredients to the skin, and further, have a poor solubility of water-insoluble pharmacologically active ingredients into the base, to thereby have a lower absorbability, because they are dispersed or suspended in the liquid phase. Many pharmacologically active ingredients assume the forms of salts, but when salts are added, the thickening property of polyacrylic acid is markedly lowered, and therefore, it is extremely difficult in practical application to formulate a pharmacologically active ingredient which takes the form of a salt (e.g., Japanese Unexamined Patent Publication (Kokai) No. 62-123112). Further, alkali metal sheets of polycarboxylic acids have a poor affinity for alcohols such as ethanol and propylene glycol, and when alcohols are to be formulated, they must be neutralized with organic amines such as diisopropanolamine, and a skilled technique is required for making the rheological characteristics of the gel uniform, whereby the steps are necessarily complicated (e.g., Japanese Unexamined Patent Publication (Kokai) No. 61-275216).

On the other hand, the plaster agent can be administered in accurate doses, and at the same time has a occlusing effect due to a backing material, and can formulate a pharmacologically active ingredient at a high concentration within a thin adhesive layer about 10 μm thick, and therefore, has an excellent absorbability of a pharmacologically active ingredient and is used for the application of a therapeutical drug agent for systemic heart diseases, such as nitroglycerine and isosorbide dinitrate. Also, in the field of surgery, various sticky bandages have been employed for fixing materials to be adhered, such as gauze and plaster cast, trauma preventers such as supporters and taping, and for the protection of the skin or the reinforcement of trauma sites.

Nevertheless, most of these plaster agents for therapy or for sticky bandages for surgery employ water-insoluble polymers such as alkyl acrylate type copolymers, styrene-isoprene copolymers, silicon type copolymers, and have serious problems in that steaming or an irritation of skin occurs because of the occulusing action thereof the skin, physical keratic peel-off due to a strong adhesion, or an allergy caused by the base ingredient (e.g., Phamacia, 7 (1), 24 (1971), Br. J. Dermatol., 112, 461 (1985), J. Invest. Dermatol., 71,378 (1978)).

As the means of alleviating the skin irritation caused by a plaster agent for therapy or a sticky bandage, to the knowledge of the present inventors, the following methods have been proposed:

1) the method of preventing a steaming eruption of the skin by enhancing the water vapor permeability of the backing material (e.g., Japanese Unexamined Patent Publications (Kokai) Nos. 54-70340, 61-210026);

2) the method of preventing a steaming eruption of skin by making the adhesive layer porous and adding a water-soluble polymeric substance such as a cellulose derivative, to thereby enhance the water vapor permeability of the adhesive layer (e.g., Japanese Unexamined Patent Publications (Kokai) Nos. 49-97058, 59-232553);

3) the method of using an adhesive having an enhanced hydrophilic property, such as acrylic copolymers having ether groups, (methacrylamide copolymers, mixtures of styrene-isoprene block copolymers and gelatin, polyoxyalkylene-modified organosiloxanes, butadiene copolymers containing -OH, -NCO groups, silicon type copolymers, etc. (e.g., Japanese Unexamined Patent Publications (Kokai) Nos. 57-85318, 59-42314, 61-187867, 62-155855, 62-263275, 63-46163, 63-66277, 1-85267, 1-99563);

4) the method of lowering the adhering force by using as the adhesive a polymer composed of fine particles (e.g., Japanese Unexamined Patent Publication (Kokai) No. 61-234865);

5) the method of lowering mechanical stimulation during the stretch-shrink effect by enhancing the stretch-shrink property of the backing material (e.g., Japanese Unexamined Patent Publication (Kokai) No. 60-75062);

6) the method of extracting low molecular weight components in the adhesive layer with an alcohol (e.g., Japanese Unexamined Patent Publication (Kokai) No. 52-75062);

7) the method of alleviating skin irritation by formulating extracts from vegetables such as Shikon, Obaku, Nanten and Kanzo, vegetable extract components such as glycyrrhizic acid, and antihistamines such as diphenhydramine (e.g., Japanese Unexamined Patent Publications (Kokai) Nos. 56-156153, 60-69016).

Even when these methods are employed, however, it is difficult to sufficiently lower the skin irritation. Further, in the plaster agent for therapy, which has been deemed to have a high absorbability of pharmacologically active ingredients, it is difficult to dissolve a water-soluble pharmacologically active ingredient in the form of a salt to a high concentration, and thus it has been difficult to effect a percutaneous absorption to the extent of obtaining a therapeutical effect on systemic diseases, except for specific pharmacologically active ingredients.

On the other hand, the bases for poultices used in the prior art for a therapy of arthritis and muscle pain are known to have a much lower skin irritation, compared with adhesives of the alkyl acrylate type, the rubber type or the silicon type. This is considered to be because the adhering force of the poultice is very weak, compared with tape agent, whereby the mechanical peel-off of skin keratin does not occur, and further, an equilibrium is established between the water vaporized from skin and the water vapor in the external atmosphere, whereby steaming eruptions can be prevented (e.g., J. Pharm. Pharmacol., 41,152 (1989)).

From such standpoints, there has been proposed a method of formulating a water-soluble polymer such as alkali metal salts of polyacrylic acid and water in alkyl acrylate type tackifiers, and a method of using a hydrous gel base containing a moisturizer such as glycerine and water as the components (e.g., Japanese Unexamined Patent Publications Nos. 60-123416, 60-99180, 61-257919, 63-238017).

In the former method, however, in the experience of the present inventors, when an alkali metal salt of polyacrylic acid is formulated in an amount which enables it to function as a hydrous base, a marked lowering in the adhesive force occurs, and thus the adhesion during plastering is often poor. In addition, since a water-soluble polymer is formulated into a non-water-soluble adhesive inherently having no compatibility, a phase separation occurs during the coating of the adhesive layer, and thus problems arise such that the moldability and working efficiency are worsened.

In poultices using an alkali metal salt of polycarboxylic acid, as represented by sodium polyacrylate of the prior art, as the thickener, because these thickeners are anionic polymers, problems arise in that they form complexes with basic pharmacologically active ingredients, as in the case of the hydrogel ointments as described above, to lower the absorbability, and that the adhering property is remarkably lowered by an addition of a salt. Further, most of these thickeners have a poor affinity for alcohols such as ethanol and propylene glycol, and thus it is difficult to formulate water-insoluble pharmacologically active ingredients to a high concentration.

Further, to obtain a sufficient adhesion to the skin, a base thickness of about 1 mm or more is generally required, thereby ensuing that not only a feeling of foreign matter or prevention to movement of the movable portion, or a defective adhesion to a movable site such as finger tip or joint may occur, but due to a difficulty in formulating pharmacologically active ingredients to high concentration, it has been also impossible to cause pharmacologically active ingredients to be absorbed to an extent such that the required effect for systemic diseases is obtained.

Thus, to the knowledge of the present inventors, there has not been obtained a base for an external application for therapy or for surgery which satisfies all requirements for a formulatability, absorbability, adhesiveness, and less skin irritation of the pharmacologically active ingredient.

On the other hand, it is known in the art that alcohols such as ethanol, isopropanol, propylene glycol, and glycerine, can enhance the percutaneous absorbability by enhancing the solubility of the pharmacologically active ingredient to the skin, or the hydration of the skin (e.g., J. Pharm, Sci., 78, 402 (1989), Pharm Tech Japan, 12, 130 (1988)).

Also, ethanol and isopropanol have sterilizing and disinfecting actions, and if these can be formulated into the adhesive, the prevention of skin irritation by bacterial proliferation as well as the effects of a sterilization and disinfection of wounded portions can be expected. Further, in a hydrous base such as a hydrogel ointment or poultice, to prevent a proliferation of mold and bacteria, it is necessary to add a preservative such as propylparaben, but propylene glycol and benzyl alcohol have the preservative actions, and glycerine and 1,3-butylene glycol alleviate skin irritation due to ethanol (e.g., Konnichino Hifugaiyozai (see, for example, Skin External Application of Today), 47 (1981)).

Nevertheless, problems arise with water-soluble polymers of the prior art when obtaining the external application base as intended by the present invention. More specifically, as mentioned above, alkali metal salts of polycarboxylic acid have a poor affinity for alcohols. As polymers soluble in water and alcohols, there are known polyvinyl pyrrolidone, hydroxypropyl cellulose, ethyl cellulose, and polyethylene glycol, but all of these have lower molecular weights than polyacrylic acid, and when used as the plastering agent, it is difficult to enhance the cohesion of the tackifier layer to the extent that no glue remains on the skin. On the other hand, polyacrylamides have relatively higher molecular weights, but have problems with respect to the safety of the human body.

On the other hand, it is difficult to add a low boiling solvent to the plaster base because heating and drying steps are included in the manufacturing process, and further, if a large amount of a solvent is added, the cohesive force will be lowered, and thus it has been impossible to add alcohols.

Thus, to the knowledge of the present inventors, there has not been obtained a polymer which has a high affinity for alcohols and can exhibit the effect of the external application base intended by the present invention.

SUMMARY OF THE INVENTION

Accordingly, the objects of the present invention are to eliminate the above-mentioned disadvantages of the prior art and to provide a base or auxiliary agent for external application for human beings or animals, which eliminates the problems of the prior art as mentioned above and exhibits a sufficient adhesion to the skin, and at the same time, has an enhanced percutaneous absorbability of a wide range of water-soluble and water-insoluble pharmacological components, and further, causes little irritation of the skin.

Other objects and advantages of the present invention will be apparent from the following description.

In accordance with the present invention, there is provided a base or an xiliary agent for external application for a human being or animal, comprising a polymer or copolymer of N-vinylacetamide or a crosslinked product thereof as the essential component.

DESCRIPTION OF THE PREFERRED EMBODIMENT

The present inventors made an intensive study of methods which can solve the problems of the base for an external application of the prior art, and consequently found that the above-mentioned object can be accomplished by using a polymer or copolymer of N-vinylacetamide or a crosslinked product thereof, to thereby complete the present invention. The present invention is described in more detail as follows.

According to the present invention, in a base or auxiliary agent for an external application for human beings or animals, preferably the composition contains a polymer or copolymer of N-vinylacetamide, as the essential component, which is a polymer or random copolymer comprising the repeating units shown by the formulae (V) - (VII) shown below [1:50 to 100 mole %, m, n: each 0 to 50 mole % (with the proviso that m+n: 0 to 50 mole %)], more preferably, having a viscosity of an aqueous 0.2% solution thereof, as measured by a Brookfield type viscometer, of 5 cps (30° C., 20 rpm) or more.

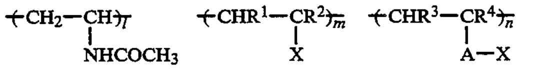 (V)

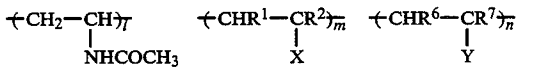 (VI)

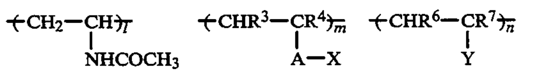 (VII wherein $R^1$ represents H, $CH_3$, $C_6H_5$ or COOM (M represents H or an alkali metal), $R^2$ represents H, $CH_3$, COOM (M is as described above), X represents COOM, $SO_3M$, $OPO_3M_2$ (M is as described above); when $R^1$ and X are COOM, the formula (II) may be also of a cyclic acid anhydride structure.

$R^3$ and $R^4$ each independently represent H, an alkyl group having 1 to 4 carbon atoms or COOM (M represents H or an alkali metal), A represents a structure shown below by (a) to (c):

$-R^5-$ (a)

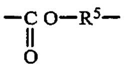 (b)

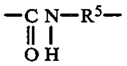 (c)

(wherein $R^5$ represents a straight or branched alkylene group having 1 to 10 carbon atoms), X represents COOM, $SO_3M$, $OPO_3M_2$ (M is as described above).

$R^6$ and $R^7$ each independently represent a hydrogen atom or an alkyl group having 1 to 4 carbon atoms, Y represents a hydrogen atom, a straight or branched alkyl group or alkenyl group having 1 to 10 carbon atoms, a methyl group with a hydrogen atom substituted with a halogen atom, a hydroxyalkyl group having 1 to 4 carbon atoms, $-CH_2NR^8R^9$ (where $R^8$ and $R^9$ each independently represent a hydrogen atom or an alkyl group or alkenyl group having 1 to 4 carbon atoms), a halogen atom, cyano group, $CH_2OCOR^{10}$ (where $R^{10}$ represents hydrogen or an alkyl group or alkenyl group having 1 to 5 carbon atoms), $COCH_3$, COOR (wherein R represents an alkyl group having 1 to 4 carbon atoms or a hydroxylalkyl group having 1 to 3 carbon atoms), $COOR^{12}NR_2{}^{13}$ (where $R^{12}$ represents an alkylene chain having 2 to 3 carbon atoms, $R^{13}$ an alkyl group having 1 to 4 carbon atoms) and a quaternary salt thereof, $COO(CH_2CH_2O)_nR^{14}$ (where $R^{14}$ represents methyl group, ethyl group, and n is an integer of 1 to 30), $CONR^{15}R^{16}$ (where $R^{15}$ and $R^{16}$ each independently represent hydrogen atom or an alkyl group or alkenyl group having 1 to 4 carbon atoms, or $CH_2OH$), $CONH-R^{12}-NR_2{}^{13}$ ($R^{12}$ and $R^{13}$ are as described above) and a quaternary salt thereof, $NR^{17}R^{18}$ (where $R^{17}$ and $R^{18}$ each independently represent an alkyl group having 1 to 4 carbon atoms), $OR^{19}$ (where $R^{19}$ represents an alkyl group or alkenyl group having 1 to 4 carbon atoms), $OCOR^{20}$ (where $R^{20}$ represents an alkyl group having 1 to 6 carbon atoms or a methyl group substituted with a halogen), phenyl group or a phenyl group nucleus-substituted with 1 to 5 of an alkyl group having 1 to 4 carbon atoms or halogen atoms, or 1 to 3 of amino group, dimethylamino group or hydroxy group, a cyclic amide represented by the formula (d) shown below:

Formula (d)

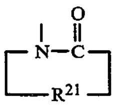 (d)

(wherein $R^{21}$ represents an alkylene chain having 3 to 7 carbon atoms) or an amide represented by the formula (e) shown below:

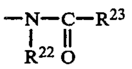
(e)

(wherein $R^{22}$ represents a hydrogen atom, methyl group, phenyl group, $R^{23}$ represents a hydrogen atom or an alkyl group having 1 to 4 carbon atoms or phenyl group).

The structural units of the (co)polymer of the present invention are now described in more detail. In the above-mentioned repeating units (V)–(VII), the structural unit represented by the following formula (II):

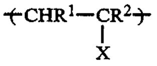
(II)

is introduced by copolymerization of the monomer described below. Namely, when X is COOM (M represents H or an alkali metal), acrylic acid, methacrylic acid, crotonic acid, maleic acid, fumaric acid, citraconic acid, cinnamic acid and salts thereof may be included, and when $R^1$ and X are COOM and the formula (II) has a cyclic acid anhydride structure, maleic anhyaride may be included.

The structural unit represented by the following formula (III):

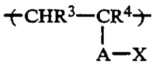
(III)

is introduced by copolymerization of the monomer as described below.

That is, when A has a structure represented by the following formula (a):

$—R^5—$ (a)

($R^5$ represents a straight or branched alkylene chain having 1 to 10 carbon atoms), examples wherein X is COOM (M represents H or an alkali metal) may include iraconic acid, aconitic acid, 3-butenoic acid, 4-pentenoic acid, ω-undecenoic acid and salts thereof, examples wherein X is $SO_3M$ (M is as described above) allylsulfonic acid, methallylsulfonic acid and salts thereof, and examples of $OPO_3M_2$ (M is as described above) allylphosphoric acid and salts thereof.

When A has the structure (b) shown below:

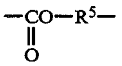
(b)

examples wherein X is COOM (M represents H or an alkali metal) may include carboxyethyl acrylate and salts thereof, examples wherein X is $OPO_3M_2$ (M is as mentioned above) 2-acryloylethylphosphoric acid, 3-acryloylpropylphosphoric acid,
4-acryloylbutylphosphoric acid,
6-acryloylhexylphosphoric acid,
8-acryloyloctylphosphoric acid,
2-methacryloylethylphosphoric acid,
3-methacryloylpropylphosphoric acid,
4-methacryloylbutylphosphoric acid,
6-methacryloylhexylphosphoric acid,
8-methacryloyloctylphosphoric acid and salts thereof.

When A has the structure (c) shown below:

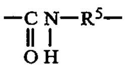
(c)

examples wherein X is COOM (M represents H or an alkali metal) may include N-methacrylic-α-amino acids and salts thereof, examples wherein X is $SO_3M$ (M is as mentioned above) 2-acrylamide-n-butanesulfonic acid, 2-acrylamide-n-propanesulfonic acid, 2-acrylamide-n-hexanesulfonic acid, 2-acrylamide-2-methylpropane sulfonic acid, and salts thereof.

The structural unit represented by the following formula (IV):

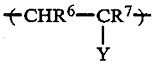
(IV)

is introduced by copolymerization of the monomers as described below. More specifically, when Y is a hydrogen atom, there may be included ethylene, propylene, isobutylene; when Y is a straight or branched alkyl group or alkenyl group, α-olefins such as 1-pentene, 2-pentene, 4-methyl-l-pentene, 1-hexene, 3-methyl-l-hexene, 4-methyl-l-hexene, 5,5-dimethyl-l-hexene and the like; when Y is a methyl group of which a hydrogen atom is substituted with a halogen atom, allyl chloride, allyl fluoride, allyl bromide, methallyl chloride, methallyl bromide, crotyl chloride, etc.; when Y is a hydroxyalkyl group having 1 to 4 carbon atoms, allyl alcohol, methallyl alcohol, crotyl alcohol, etc.; when Y is $—CH_2NR^8R^9$ (where $R^8$ and $R^9$ each independently represent a hydrogen atom or an alkyl group or alkenyl group having 1 to 4 carbon atoms), monoallylamine, methallylamine, N, N-dimethylallylamine, N, N-diethylallylamine, dimethallylamine, N-ethyldiallylamine, N-ethyldiallylamine, N, N-dimethyl-N, N-diallylamine and quaternary salts thereof, etc.

When Y is a halogen atom, there may be included vinyl chloride, vinyl fluoride, vinyl bromide and the like; when Y is cyano group, acrylonitrile, methacrylonitrile and the like; when Y is $CH_2OCOR^{10}$ (where $R^{10}$ represents a hydrogen atom, an alkyl group or alkenyl group having 1 to 5 carbon atoms), allyl esters such as allyl acetate, allyl propionate, allyl butyrate and the like; when Y is $COCH_3$, methyl vinyl ketone, methyl isopropenyl ketone, methyl propenyl ketone and the like; when Y is $COOR^{11}$ (where $R^{11}$ represents an alkyl group having 1 to 4 carbon atoms or a hydroxyalkyl group having 1 to 3 carbon atoms), methyl acrylate, ethyl acrylate, n-propyl acrylate, isopropyl acrylate, n-butyl acrylate, isobutyl acrylate, t-butyl acrylate, hydroxylethyl acrylate, hydroxypropyl acrylate, hydroxybutyl acrylate, methyl methacrylate, ethyl methacrylate, n-propyl methacrylate, isopropyl methacrylate, n-butyl methacrylate, isobutyl methacrylate, t-butyl methacrylate, hydroxyethyl methacrylate, hydroxypropyl methacrylate, hydroxybutyl methacrylate, methyl crotonate, ethyl crotonate, t-butyl crotonate, and the like.

When Y is $COOR^{12}NR_2^{13}$ (where $R^{12}$ represents an alkylene chain having 2 to 3 carbon atoms, an alkyl group having 1 to 4 carbon atoms) and a quaternary salt thereof, there may be included dimethylaminoethyl acrylate, diethylaminoethyl acrylate, dimethylaminoethyl methacrylate, diethylaminoethyl methacrylate and quaternary salts thereof; when Y is $COO(CH_2CH_2O)_nR^{14}$(where $R^{14}$ represents methyl group, ethyl group, n represents an integer of 1 to 30), diethylene glycol ethoxyacrylate, 2-ethoxyethyl acrylate, methoxypolyethylene glycol #200 methacrylate, methoxypolyethylene glycol #400 methacrylate, methoxypolyethylene glycol #1000 methacrylate, and the like.

When Y is $CONR^{15}R^{16}$ (where $R^{15}$ and $R^{16}$ each independently represent a hydrogen atom or an alkyl or alkenyl group having 1 to 4 carbon atoms, or $CH_2OH$), there may be included acrylamide, methacrylamide, N-methylacrylamide, N-methylolacrylamide, N-methylmethacrylamide, N-ethylmethacrylamide, N-n-propylacrylamide, N-methylolmethacrylamide, N,N-dimethylacrylamide; when Y is $CONH\text{-}R^{12}\text{-}NR_2{}^{13}$ ($R^{12}$ and $R^{13}$ are as described above) and a quaternary salt thereof, N,N-dimethylaminoethylacrylamide, N,N-dimethylaminoethylmethacrylamide, N,N-dimethylaminopropylacrylamide, N,N-dimethylaminopropylmethacrylamide; when Y is $NR^{17}R^{18}$ (where $R^{17}$ and $R^{18}$ each independently represent an alkyl group having 1 to 4 carbon atoms), N-vinyl-N,N-dimethylamine, N-vinyl-N-ethyl-N-butylamine; when Y is $OR^{19}$ (where $R^{19}$ represents an alkyl group or alkenyl group having 1 to 4 carbon atoms), methyl vinyl ether, ethyl vinyl ether, n-propyl vinyl ether, i-propyl vinyl ether, n-butyl vinyl ether, i-butyl vinyl ether, t-butyl vinyl ether, divinyl ether.

When Y is $OCOR^{20}$ (where $R^{20}$ represents an alkyl group having 1 to 6 carbon atoms or a methyl group substituted with a halogen atom), there may be included vinyl acetate, vinyl propionate, vinyl butyrate, trimethylacetic acid, trifluoroacetic acid; when Y is phenyl group or a phenyl group nucleus-substituted with 1 to 5 alkyl groups having 1 to 4 carbon atoms or halogen atoms, or 1 to 3 amino groups, dimethylamino groups or hydroxy groups, styrene, o-(or m-, p-)methylstyrene, 2,4-(or 2,5-, 2,6-, 3,5-)dimethylstyrene, 2,4,5-(or 2,4,6-)trimethylstyrene.

When Y is a cyclic amide represented by the following formula ( d ):

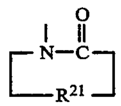

(d)

(wherein $R^{21}$ represents an alkylene chain having 3 to 7 carbon atoms), there may be included N-vinylpyrrolidone, N-vinyl-3-methylpyrrolidone, N-vinyl-5-methylpyrrolidone, N-vinyl-3,3,5-trimethylpyrrolidone, N-vinylpiperidone; when Y is an amide represented by the following formula (e):

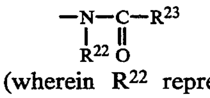

(e)

(wherein $R^{22}$ represents a hydrogen atom, methyl group, phenyl group, $R^{23}$ represents a hydrogen atom or an alkyl group having 1 to 4 carbon atoms or phenyl group), N-vinylformamide, N-vinylpropionamide, N-vinylbenzamide, N-methyl-N-vinylbenzamide, N-phenyl-N-vinylacetamide, N-phenyl-N-vinylbenzamide.

In the following, specific examples of the (co)-polymer having the repeating units shown by the above formulae (V) to (vII) are shown. Here, "partially or completely neutralized product" shows a compound in which a part or all of hydrogen ions in acidic functional groups such as carboxylic acid, sulfonic acid, phosphoric acid, etc., in the copolymer are replaced with cations of alkali metals such as sodium, potassium, or alkaline earth metals such as calcium, barium.

First, examples of the formula (V) include poly(N-vinylacetamide); N-vinylacetamide/acrylic acid copolymers and partially or completely neutralized products thereof; N-vinyl acetamide/methacrylic acid copolymers and partially or completely neutralized products thereof; N-vinylacetamide/maleic acid copolymers and partially or completely neutralized products thereof; N-vinylacetamide/fumaric acid copolymers and partially or completely neutralized products thereof; N-vinylacetamide/cinnamic acid copolymers and partially or completely neutralized products thereof; N-vinylacetamide/maleic anhydride copolymers and partially or completely neutralized products thereof; N-vinylacetamide/itaconic acid copolymers and partially or completely neutralized products thereof; N-vinylacetamide/3-butenoic acid copolymers and partially or completely neutralized products thereof; N-vinylacetamide/allylsulfonic acid copolymers and partially or completely neutralized products thereof; N-vinylacetamide/methallylsulfonic acid copolymers and partially or completely neutralized products thereof; N-vinylacetamide/allylphosphoric acid copolymers and partially or completely neutralized products thereof; N-vinylacetamide/carboxyethyl acrylate copolymers and partially or completely neutralized products thereof; N-vinylacetamide/2-acryloylethylphosphoric acid copolymers and partially or completely neutralized products thereof; N-vinylacetamide/2-acrylamide-n-propanesulfonic acid copolymers and partially or completely neutralized products thereof; N-vinylacetamide/2-acrylamide-n-octanesulfonic acid copolymers and partially or completely neutralized products thereof; 2-acrylamide-2-methylpropanesulfonic acid copolymers and partially or completely neutralized products thereof; N-vinylacetamide/methacrylic acid/itaconic acid copolymers and partially or completely neutralized products thereof; N-vinylacetamide/methacrylic acid/aconitic acid copolymers and partially or completely neutralized products thereof; N-vinylacetamide/acrylic acid/3-butenoic acid copolymers and partially or completely neutralized products thereof; N-vinylacetamide/methacrylic acid/4-pentenoic acid copolymers and partially or completely neutralized products thereof; N-vinylacetamide/acrylic acid/allylsulfonic acid copolymers and partially or completely neutralized products thereof; N-vinylacetamide/maleic acid/allylphosphoric acid copolymers and partially or completely neutralized products thereof; N-vinylacetamide/fumaric acid/carboxyethyl acrylate copolymers and partially or completely neutralized products thereof; N-vinylacetamide/methacrylic acid/2-acryloylethylphosphoric acid copolymers and partially or completely neutralized products thereof; N-vinylacetamide/methacrlic acid/3-acryloylpropylphosphoric acid copolymers and partially or completely neutralized products thereof; N-vinylacetamide/fumaric acid/2-acrylamide-n-propanesulfonic acid copolymers and partially or completely neutralized products thereof; N-vinylacetamide/cinnamic acid/2-acrylamide-n-octanesulfonic acid copolymers and partially or completely neutralized products thereof; N-vinylacetamide/acrylic acid/2-acrylamide-2-methylpropanesulfonic acid copolymers and partially or completely neutralized products thereof; and so on.

Examples of the formula (VI) include

N-vinylacetamide/propylene copolymers,

N-vinylacetamide/1-pentene copolymers,

N-vinylacetamide/methallylamine copolymers,

N-vinylacetamide/N,N-diethylallylamine copolymers,

N-vinylacetamide/vinyl chloride copolymers,

N-vinylacetamide/acrylonitrile copolymers,

N-vinylacetamide/allyl acetate copolymers,

N-vinylacetamide/methyl vinyl ketone copolymers,

N-vinylacetamide/methyl acrylate copolymers,

N-vinylacetamide/ethyl methacrylate copolymers,

N-vinylacetamide/t-butyl acrylate copolymers,

N-vinylacetamide/hydroxyethyl methacrylate copolymers,

N-vinylacetamide/hydroxypropyl methacrylate copolymers,

N-vinylacetamide/ethyl crotonate copolymers,

N-vinylacetamide/dimethylaminoethyl acrylate copolymers,

N-vinylacetamide/diethylene glycol ethoxyacrylate copolymers, N-vinylacetamide/methoxypolyethylene glycol #1000 methacrylate copolymers, N-vinylacetamide/acrylamide copolymers, N-vinylacetamide/N-methylacrylamide copolymers, N-vinylacetamide/N-methylolacrylamide copolymers, N-vinylacetamide/N,N-dimethylaminoethyl methacrylamide copolymers, N-vinylacetamide/methyl vinyl ether copolymers, N-vinylacetamide/vinyl acetate copolymers, N-vinylacetamide/styrene copolymers, N-vinylacetamide/p-methylstyrene copolymers, N-vinylacetamide/p-hydroxystyrene copolymers, N-vinylacetamide/p-aminostyrene copolymers, N-vinylacetamide/N-vinylpyrrolidone copolymers, N-vinylacetamide/N-vinylpropionamide copolymers, N-vinylacetamide/N-phenyl-N-vinyl acetamide copolymers;

N-vinylacetamide/acrylic acid/N,N-dimethylallylamine copolymers and partially or completely neutralized products thereof; N-vinylacetamide/acrylic acid-/acrylonitrile copolymers and partially or completely neutralized products thereof; N-vinylacetamide/methacrylic acid/allyl acetate copolymers and partially or completely neutralized products thereof; N-vinylacetamide/crotonic acid/methyl vinyl ketone copolymers and partially or completely neutralized products thereof; N-vinylacetamide/maleic acid/t-butyl methacrylate copolymers and partially or completely neutralized products thereof; N-vinylacetamide/acrylic acid/hydroxyethyl methacrylate copolymers and partially or completely neutralized products thereof; N-vinylacetamide/acrylic acid/hydroxypropyl methacrylate copolymers and partially or completely neutralized products thereof; N-vinylacetamide/acrylic acid/diethylaminoethyl methacrylate copolymers and partially or completely neutralized products thereof; N-vinylacetamide/fumaric acid/diethylene glycol ethoxyacrylate copolymers and partially or completely neutralized products thereof; N-vinylacetamide/acrylic acid/methoxypolyethylene glycol #1000 methacrylate copolymers and partially or completely neutralized products thereof; N-vinylacetamide/acrylic acid/acrylamide copolymers and partially or completely neutralized products thereof; N-vinylacetamide/acrylic acid/N-methylolacrylamide copolymers and partially or completely neutralized products thereof; N-vinylacetamide/methacrylic acid/N,N-diethylacrylamide copolymers and partially or completely neutralized products thereof; N-vinylacetamide/maleic acid/N,N-dimethylaminoethylmethacrylamide copolymers and partially or completely neutralized products thereof; N-vinylacetamide/methacrylic acid/methyl vinyl ether copolymers and partially or completely neutralized products thereof; N-vinylacetamide/acrylic acid/vinyl acetate copolymers and partially or completely neutralized products thereof; N-vinylacetamide/methacrylic acid/styrene copolymers and partially or completely neutralized products thereof; N-vinylacetamide/acrylic acid/N-vinylpyrrolidone copolymers and partially or completely neutralized products thereof; N-vinylacetamide/crotonic acid/N-vinylpropionamide copolymers and partially or completely neutralized products thereof; and so on.

Further, examples of the formula (VII) include N-vinylacetamide/aconitic acid/N,N-dimethylallylamine copolymers and partially or completely neutralized products thereof; N-vinylacetamide/3-butenoic acid/acrylonitrile copolymers and partially or completely neutralized products thereof; N-vinylacetamide/allylsulfonic acid/allyl acetate copolymers and partially or completely neutralized products thereof; N-vinylacetamide/allylphosphoric acid/methyl vinyl ketone copolymers and partially or completely neutralized products thereof; N-vinylacetamide/itaconic acid/methyl acrylate copolymers and partially or completely neutralized products thereof; N-vinylacetamide/itaconic acid/hydroxyethyl methacrylate copolyemers and partially or completely neutralized products thereof; N-vinylacetamide/3-butenoic acid/hydroxypropyl methacrylate copolymers and partially or completely neutralized products thereof; N-vinylacetamide/4-pentenoic acid/diethylaminoethyl methacrylate copolymers and partially or completely neutralized products thereof; N-vinylacetamide/2-acryloylethylphosphoric acid/diethylene glycol ethoxyacrylate copolymers and partially or completely neutralized products thereof; N-vinylacetamide/2-acrylamide-2-methylpropanesulfonic acid/methoxypolyethylene glycol #1000 methacrylate copolymers and partially or completely neutralized products thereof; N-vinylacetamide/itaconic acid/N-methylolacrylamide copolymers and partially or completely neutralized products thereof; N-vinylacetamide/2-acrylamide-2-methylpropanesulfonic acid/N,N-dimethylaminoethylmethacrylamide copolymers and partially or completely neutralized products thereof; N-vinylacetamide/aconitic acid/methyl vinyl ether copolymers and partially or completely neutralized products thereof; N-vinylacetamide/allylsulfonic acid/vinyl acetate copolymers and partially or completely neutralized products thereof; N-vinylacetamide/allylphosphoric acid/styrene copolymers and partially or completely neutralized products thereof; N-vinylacetamide/itaconic acid/N-vinylpyrrolidone copolymers and partially or completely neutralized products thereof; N-vinylacetamide/2-acrylamide-2-methylpropanesulfonic acid/N-vinylpropionamide copolymers and partially or completely neutralized products thereof; and so on.

The base or auxiliary agent for external application of the present invention can be suitably used in particular for ointments, plastering agents or sticky bandages. When used for ointments, the copolymer is preferably crosslinked, to inhibit stickiness to the skin, and when used for plastering agents or sticky bandages, it is necessary to crosslink the copolymer to prevent a remaining of glue on the skin, by enhancing the cohesion force. According to the present invention, a crosslinked copolymer can be obtained by carrying out a copolymerization in the co-presence of a crosslinking agent during a polymerization reaction when forming the polymer of copolymer comprising the repeating units represented by the above formulae (V) to (VII), or carrying out the known crosslinking reaction with a polyfunctional compound or a polyvalent metal ion, etc., after the polymerization reaction.

For example, there are included the method by which the compound having two or more unsaturated groups is copolymerized during polymerization reaction, including specifically ethylene glycol di(meth)acrylate, diethylene glycol di(meth)acrylate, triethylene glycol di(meth)acrylate, 1,4-butanediol diacrylate, 1,3-butanediol diacrylate, 1,6-hexanediol diacrylate, pentaerythritol triacrylate, trimethylolpropane tri(meth)acrylate, N,N'-methylenebisacrylamide, N-allylacrylamide, allyl(meth)acrylate, o(or m, p)-divinylbenzen, 1,2 ,4(or 1,3,5)-trivinylbenzene, p-allylstyrene,
N,N'-methylenebis-N-vinylacetamide,
N,N'-ethylenebis -N-vinylacetamide,
N,N'-propylenebi s-N-vinylacetamide,
N,N'-butylenebis -N-vinylacetamide,
N,N'-decylenebis -N-vinylacetamide,
N,N'-3-oxapentylenebis-N-vinylacetamide,
N,N'-3,6-dioxaoctylenebis-N-vinylacetamide,
N,N'-p-xylylenebis-N-vinylacetamide,
N,N'-diacetyl-N,N'-divinyl-1,4-bis(aminomethyl)-cyclohexane, etc., to obtain a random crosslinked product having any of the crosslinking points represented by the following formulae (VIII) [for brevity, in the following formulae, ʃ represents the polymer chain portion from which the crosslinkable functional groups are removed, R is a straight or branched alkyl group having 1 to 10 carbon atoms or polyethylene glycol chain, and $M^{n+}$represents a polyvalent metal ion]:

(VIII)

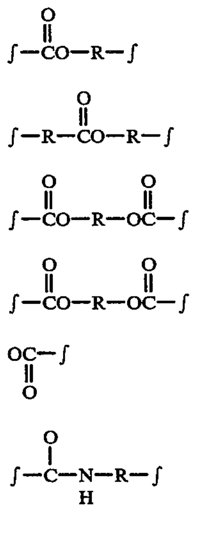

-continued

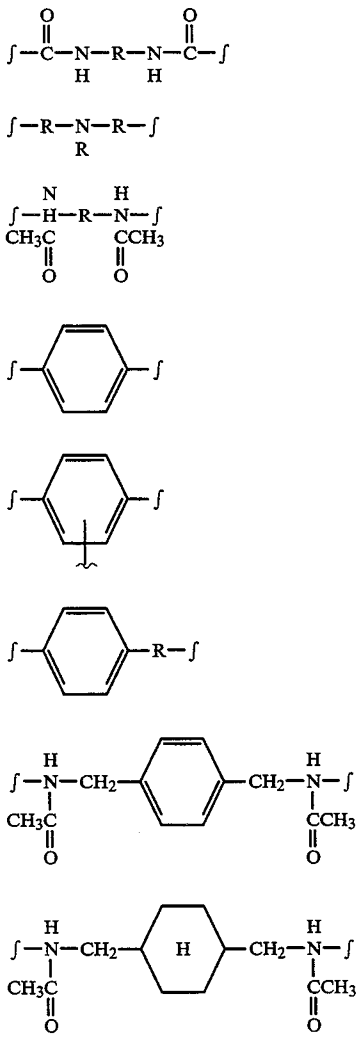

The amount of these monomers charged during polymerization is preferably 1/100 to 1/100,000 molar ratio, more preferably 1/200 to 1/50,000 molar ratio, relative to the whole amount of the monomers charged. If less than 1/100,000 molar ratio, no crosslinking effect is obtained, and if more than 1/100 molar ratio, undesirable results such as a lowering of the affinity to alcohols of the crosslinked product and a poor moldability when preparing the preparation, or a lowering of the releasability of pharmacologically active components from the preparation, will occur.

On the other hand, as the crosslinking method when preparing the preparation there are included the crosslinking reaction with radiation, light, peroxides, and the crosslinking reaction using reactive groups in the copolymer such as a hydroxy group or hydroxyalkyl group, carboxyl group, sulfonic acid group, phosphoric acid group, aminocarbonyl group, mono- or di-lower alkylaminocarbonyl group, amino group, mono- or di-lower alkylamino group.

As the crosslinking reaction using the hydroxy group and hydroxyalkyl group, there are included the method in which the copolymers containing as the above-mentioned structural unit (IV), hydroxyethyl (meth)acrylate, hydroxypropyl (meth) acrylate, hydroxybutyl (meth)acrylate, N-methylolacrylamide, (meth)allyl alcohol, crotyl alcohol, hydroxylmethyl vinyl ketone, o(or m, p)-hydroxystyrene, 2,5-dihydroxystyrene are crosslinked with the use of aldehydes such as formaldehyde, glyoxal, terephthalaldehyde, etc., for example, formaldehyde, to obtain a random crosslinked product having the crosslinking point represented by the formula (IX) with formaldehyde:

$$\int -O-CH_2-O- \int \quad (IX)$$

the method using N-methylol compounds such as N,N'-dimethylolurea, N,N'-dimethylolmelamnine, N,N'-dimethylolethyleneurea; for example, N,N'-dimethylolethyleneurea, to obtain a random crosslinked product having the crosslinking point represented by the formula (IX):

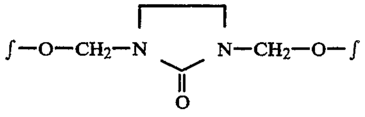
(X)

the method using dicarboxylic acids such as oxalic acid, malonic acid, succinic acid, tartaric acid, itaconic acid, fumaric acid, maleic acid, glutaric acid, and adipic acid, for example, fumaric acid, to obtain a random crosslinked product having the crosslinking point of the formula (XI):

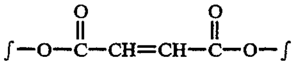
(XI)

the method of obtaining a random crosslinked product having the crosslinking point of the formula (XII) with epichlorohydrin:

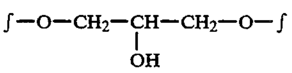
(XII)

the method of obtaining a random crosslinked product having the crosslinking point of the formula (XIII) with boric acid:

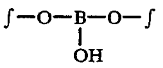
(XIII)

As the crosslinking reaction using the carboxyl group, there are included the method in which the copolymers containing as the above-mentioned structural units (II) and (III) (meth)acrylic acid, crotonic acid, fumaric acid, maleic acid, malonic acid, citraconic acid, itaconic acid, aconitic acid, vinylacetic acid, allylacetic acid, ω-undecenoic acid, carboxyethyl acrylate, N-methallyl-α-amino acid, cinnamic acid and salts thereof are copolymerized by using diamines such as ethylenediamine, N-methylethylenediamine,
N,N'-dimethylethylenediamine,
N,N'-diethylethylenediamine,
N,N'-dipropylethylenediamine,
N,N'-dibutylethylenediamine, p-phenylenediamine,
p,p'-diaminodiphenylmethane, for example, ethylenediamine, to obtain a random crosslinked product having the crosslinking point represented by the formula (XIV):

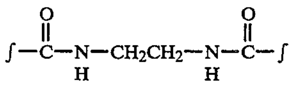
(XIV)

the method using diols such as ethylene glycol, diethylene glycol, triethylene glycol, tetraethylene glycol, for example, ethylene glycol, to obtain a random crosslinked product having the crosslinking point represented by the formula (XV):

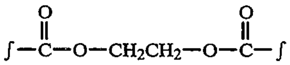
(XV)

the method using bisepoxides such as ethylene glycol diglycidyl ether, 1,1-bis (4 -glycidyloxyphenyl ) ethane, diglycidyl terephthalate, for example, ethylene glycol diglycidyl ether, to obtain a random crosslinked product having the crosslinking point of the formula (XVI);

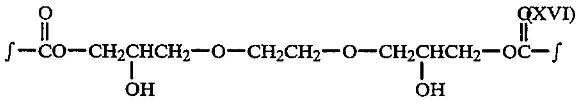
(XVI)

the method using diisocyanates such as methylene diisocyanate, ethylene diisocyanate, trimethylene diisocyanate, 1-methylethylene diisocyanate, tetramethylene diisocyanate, p-phenylene diisocyanate, p,p'-diphenylmethane diisocyanate, for example, methylene diisocyanate, to obtain a crosslinked product having the crosslinking point of the formula (XVII):

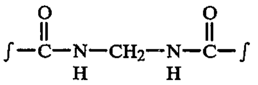
(XVII)

In the copolymers containing as the above-mentioned structural units (II) and (III), other than carboxyl groups, sulfonic acid groups such as allylsulfonic acid, methallylsulfonic acid, 2-acrylamidepropanesulfonic acid, 2-acrylamide-n-butanesulfonic acid,
2-acrylamide-n -hexanesulfonic acid,
2-acrylamide-n -octanesulfonic acid,
2-acrylamide-2 ,4,4-trimethylpentanesulfonic acid,
2-acrylamide-1 -methylpropanesulfonic acid,
3-acrylamide-3 -methylbutanesulfonic acid,
2-acrylamide-2 -methylpropanesulfonic acid, and salts thereof, etc., phosphoric acid groups such as allylphosphoric acid, 2-acryloylethylphosphoric acid,
3-acryloylpropylphosphoric acid,
4-acryloylbutylphosphoric acid,
6-acryloylhexylphosphoric acid,
8-acryloyloctylphosphoric acid,
2-methacryloylethylphosphoric acid,
3-methacryloylpropylphosphoric acid,
4-methacryloylbutylphosphoric acid,
6-methacryloylhexylphosphoric acid,
8-metacryloyloctylphosphoric acid and salts thereof, etc., there can be used the method of obtaining an ionically crosslinked product having the crosslinking point of the formula (XVIII) with a polyvalent metal compound:

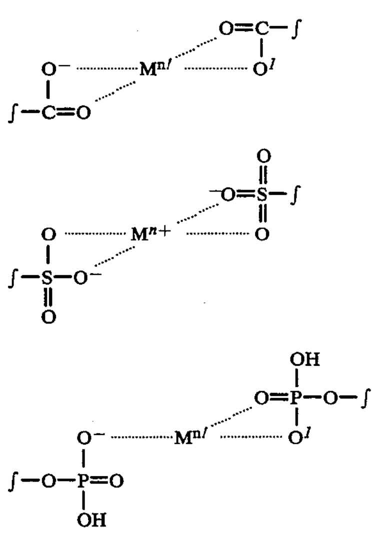

(XVIII)

or in the case of an N-vinylacetamide/acrylic acid copolymer as an example, there can be used an ionic crosslinkage with a cationic (co)polymer such as diethylsulfonic acid salt of a vinylpyrrolidone/N,N-dimethylaminoethyl methacrylate copolymer represented by the formula (XIX):

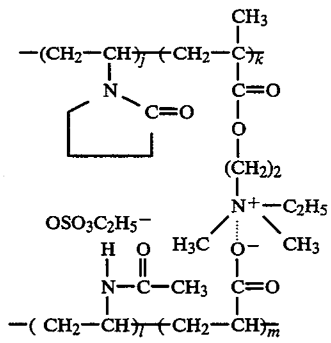

(XIX)

[J, k. l, m are positive integers (where j+k=100 mole %, 1; 50 to 99 mole %, m; 1 to 50 mole %)].

Further, in the case of copolymers containing, as the above-mentioned structural unit (III), aminocarbonyl groups such as acrylamide, methacrylamide; copolymers containing mono-lower alkylaminocarbonyl groups such as N-methylacrylamide, N-ethylacrylamide,
N-n-propylacrylamide, N-iso-propylacrylamide,
N-n-butylacrylamide, N-iso-butylacrylamide,
N-tert-butylacrylamide, N-methylolacrylamide,
N-methylmethacrylamide, N-ethylmethacrylamide,
N-t-butylmethacrylamide, N-allylacrylamide, N,N'-methylenebisacrylamide, N-acryloylacrylamide, etc.; copolymers containing di-lower alkylaminocarbonyl groups such as N,N-di-methylacrylamide, N,N-diethylacrylamide, N,N-di-iso-propylacrylamide, N,N-di-n-butylacrylamide, N,N-dimethylaminopropylacrylamide, N,N-dimethylaminopropylmethacrylamide; copolymers containing amino groups or mono- or di-lower-alkylamino groups such as monoallylamine, N,N-dimethylallylamine; copolymers containing dialkylaminoethyl (meth)acrylates such as dimethylaminoethyl arylate, diethylaminoethyl acrylate, dimethylaminoethylmethacrylate, diethylaminoethyl methacrylate, for example, in the case of an N-vinylacetamide/N,N-dimethylaminoethyl methacrylate, the ion crosslinkage with an anionic (co)polymer such as sodium polyacrylate represented by the formula (XX) can be used:

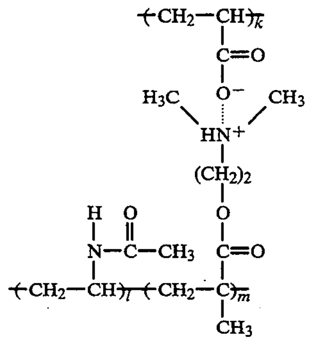

(XX)

[k, ɩ, m are positive integers (where k=100 mole %, 50 to 99 mole %, m; 1 to 50 mole %)].

Particularly, where the metal crosslinkage represented by the formula (XVIII) generally employed in the prior art for poultices is applied to the copolymer of the present invention, as the polyvalent metal compound, there are included inorganic salts, organic salts, chlorides, hydroxides, oxides of aluminum, calcium, magnesium, zinc, etc., and among them, aluminum compounds, particularly aluminum lactate, aluminum hydroxide, aluminum sulfate, aluminum potassium sulfate, aluminum ammonium sulfate, aluminum glycinate, etc. can be suitably employed.

In the case of the crosslinking reaction carried out when preparing these preparations, the amount of the crosslinking agent is preferably the range, where 5 to 20 mole % of the whole copolymer is crosslinked. If the amount is less than this range, a sufficient cohesion force can not be obtained, and with an amount more than this range, a partial gellation occurs to thereby worsen the moldability.

The characteristics of the base or auxiliary agent for an external application of the present invention are due to N-vinylacetamide copolymerized as the main monomer. Therefore, in the repeating units (V) to (VII) as described above, if the structures of (II) to (IV) comprise a ratio exceeding 50 mole %, the effects according to the present invention will be lost, resulting in a lowering of the affinity to alcohols, a poor moldability of the preparations, and a lowering of the adhesiveness, etc. When the base or auxiliary agent for an external application of the present invention is used for a plastering agent or sticky bandage, if the ratio of the structural units (II) and (III) in the repeating units of (V) to (VII) is less than 1 mole %, the crosslinking reaction will not proceed when preparing these preparations, whereby a composition having a desired mechanical strength can not be obtained. On the other hand, if these structural units exceed 50 mole %, the mutual interaction with basic pharmacologically active components will be strengthened, whereby the releasability of the pharmacologically active components from the preparations will be lowered. Further, when the viscosity of 0.2% aqueous solution of the above-mentioned copolymer measured by a Brookfield type viscometer (30° C., 20 rpm) is less than 5 cps, a liquid sag of the ointment and a worsening of the moldability of the plastering agent and the adhesive bandage will occur.

The only example of the use of N-vinylcarboxylic acid amide for the base of an external application composition is, to the knowledge of the present inventors, an example of the use of an oil-soluble copolymer with ethylene, proposed for use as the emulsified base of an ointment (e.g., Japanese Patent Publicaiton (Kokoku) No. 43-305). Nevertheless, the ratio of the N-vinylcarboxylic acid amide in the copolymer composition described is 5 to 40% by weight (1.7 t 18 mole % in the case of N-vinylacetamide), which amount adds a slight emulsifiability to polyethylene, which is inherently water-insoluble, and thus the copolymer has entirely different physical properties from the water-soluble copolymer mentioned by the present inventors. Further, there is no specific suggestion of the influence of the polymer composition on the absorbability of pharmacologically active components, etc. The polymer of an N-vinylcarboxylic acid amide, particularly a poly(N-vinylacetamide) is nonionic and a high molecular weight polymer can be easily obtained, and further, the polymer itself is readily dissolved in alcoholic solvents such as ethanol and propylene glycol. Accordingly, there can be provided an external application base composition having a better adhesiveness to the skin, water retentivity, and elasticity, with little irritation of the skin, which can formulate water-soluble and water-insoluble pharmacologically active components at high concentrations and has an excellent absorbability of pharmacologically active components. The polymer of an N-vinylcarboxylic acid amide to be used in the present invention is readily available, according to methods well known in the art (e.g., J. Am. Chem. Soc., 98, 5996 (1976), Japanese Unexamined Patent Publication (Kokai) No. 59-33312, etc.). Further, although similar effects also may be recognized when using a (co)-polymer comprising an N-vinyl-carboxylic acid amide other than N-vinylacetamide, for example, N-vinylformamide as the main invention is a readily available constituent monomer, they cannot be obtained to the extent obtained in the (co)polymer of the present invention.

As the method of preparing the polymer or the copolymer or its crosslinked product to be used in the present invention, any of the methods known in the art may be employed. For example, the polymerization can be carried out by using water or a mixture with methanol, ethanol or other organic solvents as the solvent, and a radical initiator such as an azo type compound (e.g. azobisisobutyronitrile, 2,2'-azobis-2-amidinopropane hydrochloride), a redox type initiator comprising a combination of a persulfate and an organic amine, but preferably the polymerization is carried out with the use of water as the solvent and a water-soluble azo type compound as the initiator. In some cases, the polymer also can be obtained by the W/O type reverse phase suspension polymerization in which an aqueous monomer solution is dispersed in an organic solvent, or by a precipitation polymerization. The polymerization initiation temperature depends on the initiator employed, but is preferably 0° to 100° C., more preferably 0° to 50° C. The reaction may be carried out either in air or in an inert atmosphere of nitrogen gas or argon gas, but preferably is under a nitrogen gas atmosphere. The reaction product may be solidified by the precipitation procedure, using a water-soluble solvent such as acetone, or by an evaporation of the solvent before use.

The following description is of the preparation for an external application using the (co)polymer of the present invention. First, in the present invention, to enhance the adhesiveness and water retentivity of the base composition, to increase the solubility of active ingredients, and further, to enhance the percutaneous absorbability of the pharmacologically active components, water and alcohols are formulated together with the above-described copolymer. Examples of the alcohols to be used in the present invention include at least one of saturated monovalent alcohols such as ethanol, n-propanol, iso-propanol, n-butanol, iso-butanol, sec-butanol, tert-butanol, pentanol-1, pentanol-2, pentanol-3, hexanol-1, hexanol-2, octanol-1, octanol-2, decanol-1, decanol-2, dodecanol-1, dodecanol-2, tetradecanol-1, tetradecanol-2, hexadecanol-1, hexadecanol-2, 2-hexyldecanol-1, octadecanol-1, octadecanol-2, iso-stearyl alcohol, eicosanol-1, eicosanol-2, 2-octyldodecanol-1 and the like; unsaturated monovalent alcohols such as 10-undecenol, 11-dodecenol, 12-tridecenol-1, oleyl alcohol, eraidyl alcohol, linoleyl alcohol, linolenyl alcohol and the like; polyhydric alcohols such as diethylene glycol monoethyl ether, polyethylene glycol #300, polyethylene glycol #400, polyethylene glycol #1500, polyethylene glycol #4000, polyethylene glycol #6000, propylene glycol, polypropylene glycol, 1,3-butylene glycol, glycerine, batyl alcohol, sorbitol, mannitol and the like; aromatic or cyclic alcohols such as benzyl alcohol, resorcin, phenyl ethyl alcohol, cyclohexanol, cyclononanol, cyclodecanol, cycloundecanol and the like. Particularly, those which have been used as the additives in pharmaceuticals or cosmetics may be preferably used, such as ethanol, isopropanol, dodecanol-1, hexadecanol-1, octadecanol-1, oleyl alcohol, 2-hexyldecanol-1, iso-stearyl alcohol, 2-octyldodecanol-1, propyleneglycol, 1,3-butylene glycol, glycerine, ethylene glycol monobutyl ether, polyethelene glycol (#300, #400, #1500, #4000, #6000), sorbitol, mannitol, benzyl alcohol, and combinations thereof.

Next, the pharmacologically active ingredient to be used in the present invention is not particularly limited, provided that said pharmacologically active ingredient can be percutaneously absorbed into the body when the external application is coated or plastered onto the skin. For example, there are included antiarrhythmics such as propranolol, pindolol, bupranolol, timolol; antihypertensive such as prazosin, clonidine, captopril, guanabenz; coronary vasodilators such as diltiazem, nifedipine, verapamil, nicorandil, isosorbide dinitrate, nitroglycerin; peripheral vasodilators such as isoxsuprine; cerebral vasodilators such as nicardipine, ifenprodil, vinpocetine; cardiotonics such as ubidecarenone, digoxin; diuretics such as trichlormethiazide, methyclothiazide, spironolactone, ethacrynic acid; expectorants such as bromhexine, ambroxol; antitussives such as codeine, dihydrocodeine, etc.; bronchodilators such as terbutaline, salbutamol, trimetoquinol, procaterol, fenoterol, formoterol, clenbuterol, mabuterol; antiallergics such as cromoglycic acid, ketothifen, azelastin; anticholinergics such as ipratropium; antihistaminics such as diphenhydramine, chlorphenirlamine, mequitazine, cyproheptadine, homochlorcyclizine, diphenylpyraline, clemastine; antipsychotics such as timiperone, clocapramine, haloperidol; antidepressants such as maprotiline, pipradrol; antianxiety agents such as diazepam, fludiazepam, alprazolam, clotiazepam; hypnotics agents such as triazolam, nitrazepam; antiepleptic agents such as clonazepam; skeletal muscle relaxants such as baclofen; antiperkinsonians such as biperiden, trihexyphenidyl; anti-vertigo agents such as betahistine; antispasmodics such as butropium, N-methylscopolamine, timepidium; antiemetics such as metoclopramide, domperidone, antidiabetic agents such as glibenclamide, insulin; anesthetic agents such as ethyl aminobenzoate, tetracaine, lidocaine, oxetacaine, ketamine; antiinflammatory agents such as acetaminophen, mefenamic acid, flufenamic acid, aspirin, salicylic acid, methyl salicylate, aminopyrine, antipyrine, oxyphenbutazone, sulpyrine, alclofenac, ibuprofen, ibuprofenpiconol, naproxen, flurbiprofen, ketoprofen, fenbufen, diclofenac, mepirizole, tiaramide, indomethacin, pranoprofen, piroxicam; analgesics such as pentazocine, fentanyl, bupnenorphine, butorfanol, morephine, codeine, pethidine; adrenocortical hormones such as hydrocortisone, hydrocortisone acetate, hydrocortisone butyrate, triamcinoloneacetonide, dexamethasone, dexamethasonephosphoric acid, dexamethasone acetate, betamethasone phosphate, betamethasone valerate, prednisolone, methylprednisolone succinate, flumethasone pivalate, fluocinonide, beclomethasone propionate, diflucortolone valerate, halcynonide; androges such as testosterone, testosterone propionate, testosterone enantate; estrogens and progestins such as estradiol, estradiol benzoate, estriol, progesterone, pregnanediol, chlormadinone acetate; protein anabolic steroids such as mestanolone; disinfectants such as povidone iodine, ethacridine, chlorhexidine; chemotherapeutics such as mafenide, sulfadiazine, sulfisomidine, sulfamethoxazole; antibiotics such as erythromycin, oxytetracycline, gentamicin, fradiomycin, cefalexin, fostomycin, trichomycin, variotin, nystatin; pellicle disease therapeutics such as bufexamac, crotamiton, tolnaftate, clotrimazole, isoconazole; vitamins such as retinol, alfacalcidol, thiaminepyrophosphoric acid, riboflavin tetrabutyrate, pyridoxal phosphate, nicotinic acid, pantethine, hydroxocobalamin acetate, ascorbic acid, phosphoric ascorbate, tocopherol acetate, menatetranone, phytonadione; ophthalmic agents such as pilocarpine, physostigmine, atropine, hemostatics such as carbazochromosulfonic acid, tranexamic acid; anticoagulants such as heparin, warfarin, ticlopidine; liver disease therapeutics such as thioctic acid amide, glycyrrhizinic acid; gout suppressant such as colchicine; enzyme preparations such as trypsin, chymotrypsin, bromelaine; antitumor agents such as cytarabine, 5-FU, tegafur, methotrexate, vinblastine, vincristine, mitomycin C, bleomycin, cisplatin; biological preparations such as influenzae vaccines, interferons; respiratory sitimulant such as dimefline; pituitary hormones such as desmopressin, vasopressin, oxytocin; thyroid-antithyroid hormones such as liothyronine, levothyroxine, thiamazole; metabolic drugs such as calcitonin, cyclosporin; autoimmune disease therapeutics such as azidothymidine; and pharmacologically acceptable salts of these (inorganic salts such as hydrochloride, sulfate, phosphate; organic acid salts such as lactate, citrate, tartarate, fumarate, maleate, methanesulfonate; metal salts such as sodium salt, potassium salt, calcium salt, zinc salt), and these drugs can be used either alone or as a combination of two or more thereof.

Further, to promote the absorption of the pharmacologically active ingredient from the external application composition obtained according to the present invention, there can be added absorption promoters well known in the art, such as salicylic acid, urea, dimethyl sulfoxide, n-decylmethyl sulfoxide, N-dodecylazacycloheptane-2-one, N-methyl-2-pyrrolidone, surfactants, fatty acids, or for giving a warm feeling, at least one additives such as l-menthol and capsaicin. Also, there can be optionally added additives used in the art for imparting a moldability or water retentivity of poultices, such as gelatin, kaolin, bentonite, polyvinyl pyrrolidone, sodium polyacrylate, carboxyvinyl polymer, and polyvinyl alcohol, within the range which does not interfere with the effects of the present invention.

Further, the supporting material to be used in the plastering agent of the present invention is not particularly limited, and any substance used in the art can be employed. Preferable examples include plastic films having a plasticity and are non-permeable to pharmacologically active ingredients, such as soft vinyl chloride films, polyethylene type films, ethylene copolymer films, polyester type films, polyurethane type films, polyvinyl alcohol type films, and polypropylene type films, and further, cotton cloths or nonwoven fabrics, and laminated products thereof with plastic films. Also, to enhance the anchorage between the base composition and the supporting material, a subbing agent layer having a thickness of 5 to 40 μm can be provided. As the subbing agent layer, one which can improve the adhesion between the supporting material and the base composition can be used without particular limitation, and is exemplified by an ethylene-vinyl acetate copolymer and an acrylic or rubbery pressure-sensitive adhesive.

When the (co)polymer of the present invention is formulated in the external application, in the ointment, the polymer or copolymer of N-vinylacetamide or its crosslinked product is contained preferably in an amount of from 0.5 to 10 parts by weight, more preferably 1 to 5 parts by weight, and water and/or alcohols are contained amount of from 90 to 99.5 parts by weight, preferably 95 to 99 parts by weight. If the amount of the (co)polymer or its crosslinked product is less than 0.5 part by weight, liquid sagging occurs during coating, and if more than 10 parts by weight, the viscosity is too high and this spreadability is worsened. In the plastering agent or sticky bandage, the polymer or copolymer of N-vinylacetamide or its crosslinked product is preferably from 2.5 to 33 parts by weight, more preferably from 5 to 25 parts by weight, and water and/or alcohols are preferably from 67 to 97.5 parts by weight, more preferably from 95 to 75 parts by weight. If the amount of the (co)polymer or its crosslinked product is less than 2.5 parts by weight, the mechanical strength will be lowered and if it exceeds 33 parts by weight, the solubility of the (co)polymer or its crosslinked product in a solvent will be worsened or the adhesiveness lowered. The ratio of water and/or alcohols formulated in the total formulation can be set to produced a desired solubility of the pharmacologically active ingredient to be formulated in the water and/or alcohols, and the dose, or from the viewpoint of the absorbability of the preparation of the pharmacologically active ingredient.

The amount of the pharmacologically active ingredient formulated depends on the desired therapy and/or the administration effect, but is preferably 0.001 to 10 parts by weight in the case of the ointment, and 0.01 to 30 parts by weight in the case of the plastering agent, based on 100 parts by weight of the total amount of the polymer or copolymer of N-vinylacetamide or its crosslinked product and water and/or alcohols. With amounts less than these ranges, the concentration of the pharmacologically active ingredient in the preparation is too low, and thus a sufficient absorbability can not be obtained. Conversely, if the amounts exceed these ranges, the pharmacologically active ingredient will be precipitated, to worsen the uniformity and absorbability, and the pharmacologically active ingredient will cause a plasticizing effect, whereby the spreadability of the ointment and moldability of the plastering agent will become poor.

The absorption promoter is preferably added in an amount of from 0.1 to 5% by weight of the whole preparation composition. At a level lower than this range, a desired absorption promotion effect can not be obtained, and conversely, at a level outside this range, the problem of skin irritation will occur.

The external application composition of the present invention can be prepared according to methods known in the art. For example, the above-described copolymer may be dissolved in a solvent mixture of water and alcohols, and, further according to the intended use, the pharmacologically active ingredient, crosslinking agent and, if necessary, absorption promoter and other additives formulated in the solution, followed by stirring, and, further in the case of the plastering agent or sticky bandage, the mixture spread onto a supporting material or peelable member to a thickness of 1 mm to 4 mm, then a part of the solvent evaporated to be plastered with the peelable member or the supporting material, or alternatively, the above-mentioned mixture may be spread onto a supporting material or peelable member to a thickness of 0.1 to 0.5 mm, followed by plastering with the peelable member or supporting material.

When a pharmacologically active ingredient susceptible to decomposition in a solvent is to be formulated, for example, a mixture can be prepared with an azeotropic solvent such as water/ethanol, etc., followed by a complete evaporation of the solvent, to prepare a composition, and a solvent can be added during usage.

The external application composition of the present invention, by using a (co)polymer of N-vinylacetamide in the base and further, using water and alcohols as the solvent, has the following effects, namely:

(1) an equilibrium is established between the water evaporated from skin and external water vapor, to prevent a steaming eruption of the skin;

(2) since the adhesion force is weaker than that of the alkyl acrylate type or the rubber type adhesive, a mechanical peel-off of skin keratin can be prevented;

(3) since the adhesion force is stronger than the poultice of the prior art using sodium polyacrylate as the adhesive, the base thickness can be made thinner;

(4) since a solvent mixture of water and alcohols is used, a wide range of pharmacologically active ingredients, including both water-soluble and lipied-soluble ingredients, can be formulated at high concentrations;

(5) because there are few anionic groups in the copolymer, substantially no complex formation with basic pharmacologically active ingredients occurs as in sodium polyacrylate;

(6) alcohols enhance the migratability of the pharmacologically active ingredients to the skin;

(7) water swells the skin corneum to lower the diffusion resistance of the skin to the pharmacologically active ingredients, Accordingly, it is considered that the composition can be suitably used as the external application base for therapy and surgical treatment with a low skin irritation and excellent absorbability of water-soluble and water-insoluble pharmacologically active ingredients, while possessing a sufficient adhesion force.

It is also considered that the (co)polymer of the present invention can be applied to skin external applications such as liquid coating agents or aerosols, or external preparations other than for skin (preparations for buccal, nasal, ophthalmic, rectal, vagina mucosal applications), to utilize the specific features as described above.

EXAMPLES

The present invention is now described in more detail with reference to Examples, which in no way restrict the technical scope of the present invention.

1) (Co)polymer Preparation Examples

EXAMPLES 1-20, COMPARATIVE EXAMPLES 1-3

A one-liter four-necked separable flask was equipped with a stirring rod, a thermometer and a nitrogen introducing tube, and an aqueous solution of 100 g of the starting material monomer mixture shown in Table 1 dissolved in 280 g of deionized water was charged into the flask. Thereafter, the dissolved oxygen was expelled by introducing nitrogen gas, the temperature of the solution was elevated to 30° C., 20 g of a 5% aqueous solution of 2,2'-azobis-2-amidinopropane dihydrochloride was added as the polymerization initiator, and the polymerization was carried out, while controlling the inner temperature to 30° C., for 10 hours. The polymer obtained was dehydrated by pouring into a mixture of acetone/water, followed by vacuum drying, to give a dry polymer.

One gram of the dry polymer was dissolved in distilled water to be made up to 500 ml (0.2% aqueous solution), heated to 30° C., and then the viscosity was measured by a Brookfield type viscometer at a rotational speed of 20 rpm. The results of the measurement of the viscosities are shown in Table 1. The symbols shown in Table 1 are explained below.

| | |
|---|---|
| NVA: | N-vinylacetamide |
| AA-Na: | sodium acrylate |
| AA: | acrylic acid |
| AN: | acrylonitrile |
| HPMA: | hydroxypropyl methacrylate |
| HEMA: | hydroxyethyl methacrylate |
| N-MAM: | N-methylolacrylamide |
| DAM: | dimethylaminoethyl methacrylate |
| MA: | maleic acid |
| FA: | fumaric acid |
| AMPS: | 2-acrylamide-2-methylpropanesulfonic acid |
| M-23G: | methoxypolyethylene glycol #1000 methacrylate |
| MBAM: | N,N'-methylenebisacrylamide |

TABLE 1

Preparation of (Co)polymers

| No. | (Co) polymer lot No. | Monomer composition charged (mol %) NVA | AA-Na | | Aqueous solution viscosity (cps) |
|---|---|---|---|---|---|
| Example 1 | E1 | 90 | 10 | | 287 |
| Example 2 | E2 | 80 | 20 | | 368 |
| Example 3 | E3 | 70 | 20 | AA 10 | 455 |
| Example 4 | E4 | 50 | 50 | | 597 |
| Example 5 | E5 | 80 | 10 | AN 10 | 327 |
| Example 6 | E6 | 80 | 10 | HPMA 10 | 375 |
| Example 7 | E7 | 80 | 10 | HEMA 10 | 1624 |
| Example 8 | E8 | 80 | 10 | N-MAM 10 | 654 |
| Example 9 | E9 | 90 | | DAM 10 | 56 |
| Example 10 | E10 | 80 | 10 | DAM 10 | 311 |
| Example 11 | E11 | 90 | | MA 10 | 297 |
| Example 12 | E12 | 80 | 10 | MA 10 | 374 |
| Example 13 | E13 | 90 | | FA 10 | 302 |

TABLE 1-continued

Preparation of (Co)polymers

| No. | (Co) polymer lot No. | Monomer composition charged (mol %) NVA | AA-Na | | Aqueous solution viscosity (cps) |
|---|---|---|---|---|---|
| Example 14 | E14 | 80 | 10 | AMPS 10 | 174 |
| Example 15 | E15 | 90 | | AMPS 10 | 224 |
| Example 16 | E16 | 90 | | M-23G 10 | 322 |
| Example 17 | E17 | 90 | 10 | MBAM 0.01 | 329 |
| Example 18 | E18 | 90 | 10 | MBAM 0.05 | 530 |
| Example 19 | E19 | 90 | 9.9 | MBAM 0.10 | 560 |
| Example 20 | E20 | 100 | | | 5 |
| Comparative Example 1 | C1 | 30 | 70 | | 504 |
| Comparative Example 2 | C2 | 5 | 50 | AA 45 | 602 |
| Comparative Example 3 | C3 | 0 | 70 | AA 30 | 655 |

Comparative Example 4

A two-liter four-necked separable flask was equipped with a stirring rod, thermometer, a monomer dropping funnel and a nitrogen introducing pipe, and 200 g of ethyl acetate, which was refluxed by hot water heating, was charged into the flask. Separately, a total amount of 500 g of 2-ethylhexyl acrylate, vinyl acetate, acrylic acid (80:15:5 molar ratio), and 5 g of a polymerization initiator azobisisobutyronitrile was dissolved in 150 g of ethyl acetate, the solution was added dropwise through the monomer dropping funnel into the flask, a polymerization was carried out under stirring in a nitrogen gas stream for 8 hours, and then the solid concentration was adjusted to 50% by weight with ethyl acetate to give a polymer solution (Copolymer lot No.: C4).

2) Preparation of Plastering Agent Compositions

EXAMPLES 21–37 AND EXAMPLES 46–52

An amount of 0.25 g of the copolymer having the lot No. shown in Table 2, and a predetermined amount of the pharmacologically active ingredient (DZH: diltiazem hydrochloride, DZF: diltiazem free base, NPH: nicardipine hydrochloride, PZH: prazossin hydrochloride, NC: nicorandil, SMS: sulbutamol sulfate, TP: timiperone, TZ: triazolam, MP: metoclopramide) was dissolved in 25 ml of an ethanol/water solvent mixture (5:5 to 9:1 weight ratio) at room temperature under stirring. To the solution were added 44 mg of aluminum lactate and 30 mg of sodium polyoxyethylene (4) lauryl ether phosphate dispersed in 1 g of propylene glycol, and the mixture was mixed until it became homogeneous. The mixture was then spread on a polyethylene film with a thickness of 50 μm to outer dimensions of 7×10 cm and a thickness of about 2 mm, dried at 40° C. for 4 hours, and plastered with a PET film to obtain a plastering agent composition of the present invention. The thickness of the tackifier layer was about 0.2 mm.

EXAMPLES 38–45

Into a mixture of 3.7 g of distilled water with 44 mg of lactic acid was dissolved 0.25 g of the copolymer having the lot No. shown in Table 2, at room temperature under stirring. Separately, a predetermined amount of the pharmacologically active ingredient (KPN: ketoprofen sodium salt, KPF: ketoprofen free acid) was dissolved in 1 g of propylene glycol, 23 mg of aluminum hydroxide was dispersed in the solution, and the mixture was added to the copolymer solution, followed by kneading until it became homogeneous. The kneaded product was spread on a polyethylene film with a thickness of 50 μm to outer dimensions of 7×10 cm and a thickness of about 0.5 mm, and plastered with a PET film to obtain a plastering agent composition of the present invention.

Comparative Examples 5, 6 and Comparative Examples 12–14

Using the copolymers obtained in Comparative Examples 1–3, plaster agent compositions were obtained in the same manner as in Example 21, according to the recipes shown in Table 2.

Comparative Example 9

Using the copolymers obtained in Comparative Example 1, a plastering agent composition was obtained in the same manner as in Example 43, according to the recipe shown in Table 2.

Comparative Example 7

To 4.2 g of glycerine heated to 60° C. were added 1.2 g of sodium polyacrylate and 0.2 g of aluminum hydroxide was dispersed therein under stirring for one hour. Then to the dispersion was added a solution of 90 mg of diltiazem hydrochloride and 30 mg of sodium polyoxyethylene (4) lauryl ether phosphate dissolved in 2 g of a propylene glycol/water solvent mixture (1:1 weight ratio), followed by mixing under stirring. After the mixture was cooled to 50° C. or lower, a liquid prepared separately by swelling a carboxyvinyl polymer (Carbopol 934) with 4.2 g of distilled water was added, and the mixture was kneaded until it became homogeneous. The kneaded product was spread on a polyethylene film with a thickness of 50 μm to outer dimensions of 7×10 cm and a thickness of about 1 mm, and plastered with a PET film to obtain a poultice-like composition.

Comparative Examples 8, 10

Into 40 g of the copolymer solution obtained in Comparative Example 4 was added 9 g of diltiazem hydrochloride or 3 g of ketoprofen free acid as a suspension or solution in 3 g of ethyl acetate, followed by stirring. The liquid was coated on a silicon-treated PET film with a thickness of 120 μm, dried at 100° C. for 3 minutes, and then plastered with a polyethylene film with a thickness of 50 μm to obtain a plaster-like composition. The thickness of the tackifier layer was about 40 μm.

Comparative Example 11

In place of the plastering agent of the present invention, a commercially available poultice (outer dimensions: 10×14 cm) containing ketoprofen was employed.

TABLE 2

Preparation of plastering agent compositions

| No. | Co-polymer lot No. | (g) | Pharmacologically active ingredient | (mg) | Dosage form |
|---|---|---|---|---|---|
| Example 21 | E1 | 0.25 | DZH | 90 | Plastering agent |
| Example 22 | E4 | 0.25 | " | 90 | " |
| Example 23 | E5 | 0.25 | " | 90 | " |
| Example 24 | E6 | 0.25 | " | 90 | " |
| Example 25 | E8 | 0.25 | " | 90 | " |

TABLE 2-continued

| Preparation of plastering agent compositions | | | | | |
|---|---|---|---|---|---|
| No. | Co-polymer lot No. | (g) | Pharmacologically active ingredient | (mg) | Dosage form |
| Example 26 | E11 | 0.25 | " | 90 | " |
| Example 27 | E12 | 0.25 | " | 90 | " |
| Example 28 | E13 | 0.25 | " | 90 | " |
| Example 29 | E15 | 0.25 | " | 90 | " |
| Example 30 | E1 | 0.25 | DZF | 90 | " |
| Example 31 | E4 | 0.25 | " | 90 | " |
| Example 32 | E5 | 0.25 | " | 90 | " |
| Example 33 | E14 | 0.25 | " | 90 | " |
| Example 34 | E15 | 0.25 | " | 90 | " |
| Example 35 | E17 | 0.25 | " | 90 | " |
| Example 36 | E18 | 0.25 | " | 90 | " |
| Example 37 | E19 | 0.25 | " | 90 | " |
| Example 38 | E1 | 0.25 | KPN | 30 | " |
| Example 39 | E4 | 0.25 | KPN | 30 | Plastering agent |
| Example 40 | E5 | 0.25 | " | 30 | " |
| Example 41 | E7 | 0.25 | " | 30 | " |
| Example 42 | E19 | 0.25 | " | 30 | " |
| Example 43 | E1 | 0.25 | KPF | 30 | " |
| Example 44 | E5 | 0.25 | " | 30 | " |
| Example 45 | E19 | 0.25 | " | 30 | " |
| Example 46 | E1 | 0.25 | NPH | 30 | " |
| Example 47 | E1 | 0.25 | PZH | 5 | " |
| Example 48 | E1 | 0.25 | NC | 45 | " |
| Example 49 | E1 | 0.25 | SMS | 12 | " |
| Example 50 | E1 | 0.25 | TP | 12 | " |
| Example 51 | E1 | 0.25 | TZ | 2 | " |
| Example 52 | E1 | 0.25 | MP | 30 | " |
| Comparative Example 5 | C1 | 0.25 | DZH | 90 | " |
| Comparative Example 6 | C2 | 0.25 | " | 90 | " |
| Comparative Example 7 | C3 | 1.2 | " | 90 | Poultice |
| Comparative Example 8 | C4 | 0.20 | " | 90 | Plaster agent |
| Comparative Example 9 | C1 | 0.25 | KPF | 30 | Plastering agent |
| Comparative Example 10 | C4 | 0.20 | KPF | 30 | Plaster agent |
| Comparative Example 11 | Commercially available Poulice | | " | 30 | Poulice |
| Comparative Example 12 | C3 | 1.2 | NPH | 30 | " |
| Comparative Example 13 | C3 | 1.2 | PZH | 5 | " |
| Comparative Example 14 | C3 | 1.2 | SMS | 12 | " |

3) Preparation of Ointment-like Compositions

EXAMPLES 53-63

An amount of 0.3 g of the (co)polymer with the lot No. shown in Table 3 was dissolved at room temperature under stirring in 4.7 g of a solvent mixture of propylene glycol/ethanol/water (1:1:2.7 weight ratio). Then the solution was added a solution of a predetermined amount of the pharmacologically active ingredient dissolved in 4 g of an ethanol/water solvent mixture (1:1 weight ratio) and the mixture was stirred until the whole became homogeneous, to obtain an ointment-like composition of the present invention.

Comparative Examples 15, 16, 18

Using the copolymers prepared in Comparative Examples 1, 2, ointment-like compositions were obtained according to the same method as in Example 53, following the recipes shown in Table 3.

Comparative Examples 17, 19

To a solution of 50 mg of diisopropanolamine dissolved in 4.55 g of distilled water was added 0.2 g of carboxyvinyl polymer (Carbopol 934) and stirred at room temperature to be swollen therewith, then a solution was added of a predetermined amount of the pharmacologically active ingredient, according to the recipe shown in Table 3, and 0.2 g of hydroxypropyl cellulose dissolved at room temperature in 4 g of an ethanol/water solvent mixture (1:1 weight ratio), followed by stirring until the whole became homogeneous, to obtain an ointment-like composition.

TABLE 3

| Preparation of Ointment-like Compositions | | | | | |
|---|---|---|---|---|---|
| No. | Copolymer lot No. | (g) | Pharmacologically active ingredient | (mg) | Dosage form |
| Example 53 | E1 | 0.3 | DZH | 1.0 | Ointment |
| Example 54 | E4 | 0.3 | " | 1.0 | " |
| Example 55 | E9 | 0.3 | " | 1.0 | " |
| Example 56 | E10 | 0.3 | " | 1.0 | " |
| Example 57 | E16 | 0.3 | " | 1.0 | " |
| Example 58 | E19 | 0.3 | " | 1.0 | " |
| Example 59 | E20 | 0.3 | " | 1.0 | " |
| Example 60 | E1 | 0.3 | KPF | 1.0 | " |
| Example 61 | E4 | 0.3 | " | 1.0 | " |
| Example 62 | E16 | 0.3 | " | 1.0 | " |
| Example 63 | E20 | 0.3 | " | 1.0 | " |
| Comparative Example 15 | C1 | 0.3 | DZH | 1.0 | |
| Comparative Example 16 | C2 | 0.3 | " | 1.0 | " |
| Comparative Example 17 | CVP + HPC | 0.4 | " | 1.0 | " |
| Comparative Example 18 | C2 | 0.3 | KPF | 1.0 | " |
| Comparative Example 19 | CVP + HPC | 0.4 | " | 1.0 | " |

4) Solubility of (Co)polymer in Alcohols

Evaluation Example 1

The (co)polymers prepared in Examples 1 and 20 and Comparative Example 1 were added in an amount of 0.5 g in various solvents (Gly: glycerine, EtOH: ethanol, PG: propylene glycol, BG: 1,3-butylene glycol) at the concentrations shown in Table 4 (1 or 10% by weight), heated at 40° C. for 48 hours, then left to cool to room temperature, and the appearances thereof were observed.

Next, to 0.5 g of each (co)polymer prepared in Examples 1 to 20 and Comparative Examples 1, 3 was added 4.5 g of ethanol/water (1:1 weight ratio), the mixture was heated at 40° C. for 48 hours, left to cool to room temperature, and the appearance then observed. When the (co)polymer was not dissolved, 5 to 10 g of the solvent was successively added to repeat the heating operation, and the solubility was determined by observation of the appearance. The lower limit of the (co)-polymer concentration was made 0.1%.

As the result, as shown in Table 4, in the (co)polymers of N-vinylacetamide and acrylic acid (sodium), the homopolymer of N-vinylacetamide (Example 20) and the copolymer containing 90 mole % of N-vinylacetamide (Example 1) was confirmed to have an extremely higher solubility in alcohols and solvent mixtures of alcohols/water than the copolymer containing 5 mole % of the N-vinylacetamide (Comparative Example 2).

Similarly, as shown in Table 5, the (co)polymers containing 50 mole % or more of N-vinylacetamide (Examples 1–4 and 20), the copolymers partially pre-crosslinked with methylene-bis-acrylamide (Examples 17–19), and further, the binary or ternary copolymers of 80 to 90 mole % of N-vinylacetamide with various copolymer components (Examples 5–16), have markedly higher solubilities in ethanol/water solvent mixture (1:1 weight ratio) than the copolymer with 30 mole % of N-vinylacetamide (Comparative Example 1) and sodium polyacrylate (Comparative Example 3), and it was confirmed that the (co)polymer of the present invention has a greater affinity for alcohols than the sodium polyacrylate generally employed for the base of external application of the prior art.

TABLE 4

Solubility in Alcohols (1)

| | Example 1 | | Example 20 | | Comparative Example 2 | |
|---|---|---|---|---|---|---|
| Solvent | Amount added | State | Amount added | State | Amount added | State |
| Gly | 1% | Δ | 1% | Δ | 1% | x |
| 50% EtOH/water | 10% | ∘ | 10% | ∘ | 0.1% | x |
| 50% PG/water | 10% | ∘ | 10% | ∘ | 0.1% | ∘ |
| 50% BG/water | 10% | ∘ | 10% | ∘ | 0.1% | x |
| 50% Gly/water | 10% | ∘ | 10% | ∘ | 0.5% | ∘ |

∘; completely dissolved
Δ; substantially dissolved
x; undissolved

TABLE 5

Solubility in alcohols (2)

| No. | 50% EtOH/water solubility (wt %) |
|---|---|
| Example 1 | ≧10 |
| Example 2 | 10–6.7 |
| Example 3 | 5 |
| Example 4 | 3.3–2.5 |
| Example 5 | 2.5–2 |
| Example 6 | 1.5–1.0 |
| Example 7 | 4–3.3 |
| Example 8 | 3.3–2.5 |
| Example 9 | 3.3–2.5 |
| Example 10 | 3.3–2.5 |
| Example 11 | 10–5 |
| Example 12 | 5–3.3 |
| Example 13 | 5–3.3 |
| Example 14 | 5–3.3 |
| Example 15 | 10–5 |
| Example 16 | 5–3.3 |
| Example 17 | 5–3.3 |
| Example 18 | 5–3.3 |
| Example 19 | 3.3–2.5 |
| Example 20 | ≧10 |
| Comparative Example 1 | 0.6–0.5 |
| Comparative Example 3 | <0.1 |

Evaluation Example 2

First, 0.25 g each of N-vinylacetamide/sodium acrylate copolymers with different compositions (Examples 1–4, Comparative Example 1) and sodium polyacrylate (Comparative Example 3) were dissolved under stirring in 19.75 g of distilled water at room temperature. As an example of a basic pharmacologically active ingredient, 0.5 g of diltiazem hydrochloride was dissolved in 2.0 g of distilled water, the aqueous solution was added to an aqueous copolymer solution under stirring, and the change in appearance was observed.

As a result, as shown in Table 6, in sodium polyacrylate (Comparative Example 3) and the copolymer with 30 mole % of N-vinylacetamide (Comparative Example 1), turbidity and agglomeration reaction, which may be considered to be due to complex formation between the carboxyl groups in the copolymer and diltiazem, were observed. On the other hand, in the copolymer with 50 mole % or more of N-vinylacetamide (Examples 1–4), the extent of change in the appearance was lessened as the ratio of sodium acrylate was reduced. Therefore, it was clear that the copolymer of the present invention has a lower mutual interaction with the basic pharmacologically active ingredient than sodium polyacrylate.

TABLE 6

Complex formation with basic pharmacologically active ingredient

| No | Appearance |
|---|---|
| Example 1 | Transparent |
| Example 2 | Slightly suspended |
| Example 3 | Suspended |
| Example 4 | Turbid |
| Comparative Example 1 | Turbid, agglomerated |
| Comparative Example 3 | Turbid, agglomerated |

Evaluation Example 3

For the plastering agent compositions prepared in Examples 21–29, 33 and 35–37, the moldability and adhesion force were measured of the poultice prepared in Comparative Example 7, the commercially available poultice used in Comparative Example 11, and the plaster agent prepared in Comparative Example 8.

The moldability was judged from the stickiness of the tackifier layer, by finger touch, and the presence or absence of agglomeration breaking in the probe tack test shown below. The adhesion force was evaluated by the probe tack test and the plastering test onto the human skin. The probe tack test was carried out by using a stainless steel probe as the body to be adhered, and measuring the force at which the probe was peeled from the adhered surface under the conditions of a moving speed of the probe of 10 mm/sec. and a contact time of 1 sec. The plastering test onto the human skin was performed by plastering a sample with dimensions of 3×7 cm onto the forearm portion skin for 6 hours, and the adhesiveness during plastering was evaluated.

As the result, as shown in Table 7, the moldability was good for all the samples, but for the adhesion force, substantially no probe tacking force was exhibited by poultices (Comparative Examples 7, 11), and the adhesiveness to skin was bad. The plaster agent (Comparative Example 8) exhibited the highest tacking force, and pain occurred when it was peeled from the skin, and surface skin peel-off onto the sticking surface was observed. On the other hand, the plastering agent compositions of the present invention (Examples 21–29, 33, 35–37) exhibited adhesion forces between those of the poultice and the plaster agent, without any peel-off during plastering or irritation during peel-off.

TABLE 7

Moldability, tackiness of plastering agent compositions

| No. | Moldability | Probe tack force (gf) | Skin adhesion |
|---|---|---|---|
| Example 21 | Good | 41 | Good |
| Example 22 | " | 95 | " |

TABLE 7-continued

| | Moldability, tackiness of plastering agent compositions | | |
|---|---|---|---|
| No. | Moldability | Probe tack force (gf) | Skin adhesion |
| Example 23 | " | 72 | " |
| Example 24 | " | 69 | " |
| Example 25 | " | 28 | " |
| Example 26 | " | 68 | " |
| Example 27 | " | 126 | " |
| Example 28 | " | 71 | " |
| Example 29 | " | 143 | " |
| Example 33 | " | 87 | " |
| Example 35 | " | 29 | " |
| Example 36 | " | 44 | " |
| Example 37 | " | 42 | " |
| Comparative Example 7 | " | 0 | Poor |
| Comparative Example 11 | " | 0 | " |
| Comparative Example 8 | " | 293 | Strongly stuck |

7) Appearance and Feeling of Ointment When Used:

Evaluation Example 4

The appearance of the ointment-like compositions prepared in Examples 53–59 and Comparative Examples 15–17, and the use feeling (spreadability, tackiness) when each 0.2 g was coated on the human forearm portion were evaluated.

As a result, as shown in Table 8, in the compositions using copolymers containing 70 and 95 mole % of sodium acrylate (Comparative Examples 15, 16) and the composition using a carboxyvinyl polymer (Comparative Example 17), a white suspended product or an agglomerate was formed when the diltiazem solution was added to the polymer solution. In these compositions, a separation of the liquid phase was observed after standing, and the use feeling on the skin was poor during use. Such an agglomeration reaction also may be considered to be due to a complex formation between the carboxyl groups in the polymer and diltiazem similarly, as in the result of Evaluation Example 2.

On the other hand, in the compositions of the present invention (Examples 53–59), although a slight whitening was observed in Example 54, there was no agglomeration reaction and homogeneous compositions could be obtained. The feeling during use on the skin was good, and the removal by washing with water was accomplished with ease.

TABLE 8

| | Appearance, use feeling of ointment-like compositions | |
|---|---|---|
| No. | Appearance | Use feeling |
| Example 53 | Transparent | Good |
| Example 54 | White translucent | " |
| Example 55 | Transparent | " |
| Example 56 | " | " |
| Example 57 | " | " |
| Example 58 | " | " |
| Example 59 | " | " |
| Comparative Example 15 | White suspension | Slightly poor |
| Comparative Example 16 | White agglomeration | Poor |
| Comparative Example 17 | White agglomeration | Poor |

8) Releasability of Pharmacologically Active Ingredient from Plastering Agent Composition:

Evaluation Example 5

The plastering agent compositions prepared in Examples 21–49 and Comparative Examples 5, 6, 9, the poultices prepared in Comparative Examples 7, 12–14, the commercially available poultice used in Comparative Example 11, and the plastering agents prepared in Comparative Examples 8, 10 were evaluated for the releasability of the pharmacologically active ingredients therefrom.

The paddle of an elution tester listed in the Japanese Pharmacopoeia was mounted to a plastic vessel, on which was fixed a sample of 7×5 cm with a double-coated tape with the sticky surface on the outside, which was rotated at a rotational speed of 50 rpm, while using one liter of a 50 mM phosphate buffer (pH 5.5) maintained at 37° C. as the eluant, to release the pharmacologically active ingredient. At predetermined times, one ml of the eluate was sampled, filtered through a 45 μm membrane filter, the absorbance at 254 nm was measured by a spectrophotometer, and the released amount was determined from the absorbance ratio to the known concentration of the pharmacologically active ingredient. From the released amount, the time required for release of 50% of the pharmacologically active ingredient relative to the final released amount after 24 hours (50% release time), and the ratio of the final released amount relative to the amount of the pharmacologically active ingredient formulated in the composition (release ratio), were calculated.

The results are shown in Table 9. In the case of diltiazem, which is a basic pharmacologically active ingredient, in the compositions of the plastering agent compositions of the present invention (Examples 21–37), both the water soluble hydrochlorides and water-insoluble free bases can be formulated when dissolved, and at the same time, the 50% release time was about 0.3 to 0.5 hour, regardless of the composition of the copolymer employed, and the release ratio also was good. On the other hand, in the compositions using the copolymers with ratios of sodium acrylate of 70 and 95 mole % (Comparative Examples 5, 6), and the poultice using sodium polyacrylate (Comparative Example 7), a prolonging of the release time and lowering of the release ratio were recognized with an increase of the amount of acrylic acid formulated, and the release time was prolonged by about 10-fold and the release ratio lowered by about ½ in poultices. Similar results were obtained in the cases of the use of nicardipine hydrochloride, prazosin hydrochloride, salbutamol sulfate (Examples 46–49 and Comparative Examples 12–14).

No difference could be seen in the release time and release ratio of the plaster agent (Comparative Example 8).

Therefore, when combined with the results in Evaluation Example 2, it may be considered that the interaction between the carboxyl groups in the copolymer and the basic pharmacologically active ingredient lowers the releasability, whereby it is confirmed that the composition of the present invention with few anionic groups has an excellent releasability of the basic pharmacologically active ingredient.

On the other hand, even in ketoprofen, which is an acidic pharmacologically active ingredient, the compositions of the present invention (Examples 38–45) could be formulated when dissolved for both water-soluble sodium salts and water-insoluble free acids, but for the releasability of the pharmacologically active ingredient, there was substantially no difference in any of the cases using the copolymer containing 70 mole % of sodium acrylate (Comparative Example 9), the commercially available poultice (Comparative Example 11), and the plaster agent (Comparative Example 10).

TABLE 9

Releasability of pharmacologically active ingredient from plastering agent compositions

| No. | Pharmacologically active ingredient | Release time (hr) | Release ratio (%) |
|---|---|---|---|
| Example 21 | DZH | 0.28 | 98 |
| Example 22 | " | 0.55 | 97 |
| Example 23 | " | 0.35 | 98 |
| Example 24 | " | 0.56 | 97 |
| Example 25 | " | 0.27 | 95 |
| Example 26 | " | 0.33 | 96 |
| Example 27 | " | 0.35 | 94 |
| Example 28 | " | 0.26 | 91 |
| Example 29 | " | 0.48 | 88 |
| Example 30 | DZF | 0.26 | 95 |
| Example 31 | " | 0.52 | 87 |
| Example 32 | " | 0.36 | 95 |
| Example 33 | " | 0.30 | 97 |
| Example 34 | " | 0.42 | 94 |
| Example 35 | " | 0.28 | 96 |
| Example 36 | " | 0.26 | 99 |
| Example 37 | " | 0.41 | 97 |
| Example 38 | KPN | 0.84 | 95 |
| Example 39 | " | 0.81 | 89 |
| Example 40 | KPN | 0.93 | 97 |
| Example 41 | " | 0.76 | 95 |
| Example 42 | " | 1.04 | 97 |
| Example 43 | KPF | 0.64 | 96 |
| Example 44 | " | 0.84 | 91 |
| Example 45 | " | 0.69 | 95 |
| Example 46 | NPH | 0.29 | 97 |
| Example 47 | PZH | 0.38 | 88 |
| Example 49 | SMS | 0.33 | 91 |
| Comparative Example 5 | DZH | 1.03 | 97 |
| Comparative Example 6 | " | 3.82 | 59 |
| Comparative Example 7 | " | 4.13 | 51 |
| Comparative Example 8 | " | 0.18 | 98 |
| Comparative Example 9 | KPF | 0.68 | 92 |
| Comparative Example 10 | " | 0.95 | 97 |
| Comparative Example 11 | " | 1.16 | 94 |
| Comparative Example 12 | NPH | 4.52 | 28 |
| Comparative Example 13 | PZH | 5.11 | 34 |
| Comparative Example 14 | SMS | 4.77 | 45 |

9) Absorbability of Pharmacologically Active Ingredient in Rabbit:

Evaluation Example 6

The plastering agent compositions prepared in Examples 21–24, and 43–45 and Comparative Example 5, the poultice prepared in Comparative Example 7, the commercially available poultice used in Comparative Example 11, the plaster agents prepared in Comparative Examples 8, 10, and the ointment-like compositions prepared in Examples 53, 54 and 60 and Comparative Examples 17 and 19 were evaluated for absorbability of the pharmacologically active ingredient in rabbit.

On the back skin of a rabbit depilated with electrical clippers and a depilation cream on the day before the test, a plastering agent composition with dimensions of 7×10 cm or one gram of an ointment-like composition was plastered or coated, and fixed by covering the flank portion with gauze or a sticky stretchable bandage. At predetermined times, 2.5 ml of blood was sampled from the auricle vein, and a plasma was obtained by centrifugation.

An analysis of diltiazem in the plasma was carried out by the method described below. To 0.5 ml of plasma was added 50 μl of an internal standard substance (5 μg/ml aqueous verapamil solution), and after partition with 5 ml of t-butyl methyl ether, the ether phase was separated by centrifugation, 0.2 ml of 0.1N sulfuric acid was added, the mixture was subjected to reverse extraction, and the pharmacologically active ingredient concentration was measured by high performance liquid chromatography.

The analysis of ketoprofen in the plasma was carried out by the method described below. To 0.5 ml of plasma were added 50 μl of an internal standard substance (100 μg/ml of aqueous flurbiprofen solution), 0.2 ml of 0.5N hydrochloric acid, and 100 mg of sodium chloride, and after partition with 3 ml of ethyl acetate, the ethyl acetate was separated by centrifugation. This partition operation was repeated 3 times, 9 ml of the ethyl acetate was evaporated under a reduced pressure at 45° C., the residue dissolved by an addition of 0.5 ml of methanol, and the concentration of the pharmacologically active ingredient measured by high performance liquid chromatography.

The results are shown in Table 10. In both the diltiazem hydrochloride, which is a water-soluble pharmacologically active ingredient, and a water-insoluble ketoprofen, the absorbability of the plastering agent compositions according to the present invention (Examples 21–24, and 43–45) is clearly better than that of the poultices (Comparative Examples 7, 11), and is comparable with that of the plaster agents (Comparative Examples 8, 10) which are deemed to have a high absorbability in the prior art. Similarly, in ointment-like compositions, it was shown that the compositions according to the present invention (Examples 53, 54, 60) have a better absorbability than the compositions using the carboxyvinyl polymer (Comparative Examples 17, 19). These effects, as shown in Evaluation Examples 2 and 5, may occur because the interaction between the (co)-polymer of the present invention and a basic pharmacologically active ingredient is small, whereby the releasability of the phamacologically active ingredient from the composition is excellent; that the thickness of the plastering agent is thinner than poultices, and thus the pharmacologically active ingredient can be formulated at higher concentration; and that the absorption promotion effect by alcohols can be utilized.

From the evaluation results as described above, it is clear that the base composition for external application according to the present invention has a sufficient adhesive force to the skin, and alleviates irritation of the skin, enhances the absorbability of a wide range of water-soluble and water-insoluble pharmacologically active ingredients, and thus has excellent characteristics as the base or auxiliary agent for external application.

TABLE 10

Absorbability of pharmacologically active ingredients in rabbit

| No. | Pharmacologically active ingredient | Dosage form | Level of pharmacologically active ingredient in blood (μg/ml) 1 hr | 2 hr | 4 hr | 8 hr | 24 hr | AUC μg · hr/ml |
|---|---|---|---|---|---|---|---|---|
| Example 21 | Diltiazem hydrochloride | Plastering agent | 24 | 66 | 108 | 122 | 67 | 2.2 |
| Example 22 | " | " | 13 | 24 | 48 | 71 | 60 | 1.4 |
| Example 24 | " | " | 22 | 48 | 78 | 94 | 63 | 1.8 |
| Comparative Example 5 | " | " | 6 | 17 | 20 | 22 | 20 | 0.6 |
| Comparative Example 7 | " | Poultice | 4 | 6 | 6 | 7 | 6 | 0.2 |
| Comparative Example 8 | " | Plastering agent | 71 | 134 | 137 | 114 | 43 | 2.1 |
| Example 43 | Ketoprofen free acid | Plastering agent | 360 | 640 | 900 | 830 | 540 | 16.6 |
| Example 44 | " | " | 185 | 400 | 610 | 680 | 400 | 12.6 |
| Example 45 | " | " | 290 | 510 | 770 | 710 | 420 | 13.8 |
| Comparative Example 10 | " | Plaster agent | 138 | 478 | 842 | 832 | 396 | 13.1 |
| Comparative Example 11 | " | Poultice | 76 | 204 | 272 | 174 | 40 | 2.8 |
| Example 53 | Diltiazem hydrochloride | Ointment | 62 | 110 | 148 | 87 | 12 | 1.6 |
| Example 54 | " | " | 33 | 64 | 90 | 55 | 9 | 1.0 |
| Comparative Example 17 | " | " | 5 | 7 | 10 | 8 | 5 | 0.2 |
| Example 60 | Ketoprofen free acid | " | 300 | 440 | 540 | 380 | 180 | 5.2 |
| Comparative Example 19 | " | " | 50 | 90 | 150 | 120 | 90 | 2.6 |

We claim:

1. A base or an auxiliary agent for external application for a human being or animal, comprising a polymer or copolymer of N-vinylacetamide having a structure containing 50 to 100 mole % of the repeating unit represented by the formula (I) and 0 to 50 mole % of at least one kind of the repeating units represented by the formula (II):

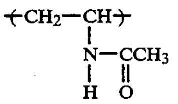
(I)

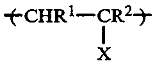
(II)

wherein $R^1$ represents H, $CH_3$, $C_6H_5$, or COOM, wherein M represents H or an alkali metal; $R^2$ represents H, $CH_3$, COOM; and X represents COOM; when $R^1$ and X are COOM, the formula (II) also may have a cyclic acid anhydride structure.

2. A base or an auxiliary agent for external application for a human being or animal according to claim 1, wherein said polymer contains, as the essential component, a crosslinked polymer having a structure crosslinked: (1) by copolymerization in the presence of a crosslinking agent during the polymerization reaction for forming said polymer, or (2) by crosslinking with a polyfunctional compound or a polyvalent metal ion after a polymerization reaction.

3. A base or auxiliary agent for external application according to claim 1, wherein the polymer or copolymer of N-vinylacetamide has a viscosity of 5 cps or more, at 30° C. and 20 rpm, in a 0.2% aqueous solution, as measured by a Brookfield type viscometer.

* * * * *